(12) United States Patent
Lin et al.

(10) Patent No.: US 6,906,181 B2
(45) Date of Patent: Jun. 14, 2005

(54) METHUSELAH GENE, COMPOSITIONS AND METHODS OF USE

(75) Inventors: Yi-Jyun Lin, Arcadia, CA (US); Seymour Benzer, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 227 days.

(21) Appl. No.: 09/978,486

(22) Filed: Oct. 15, 2001

(65) Prior Publication Data

US 2002/0052015 A1 May 2, 2002

Related U.S. Application Data

(62) Division of application No. 09/370,098, filed on Aug. 6, 1999, now Pat. No. 6,303,768
(60) Provisional application No. 60/095,826, filed on Aug. 7, 1998.

(51) Int. Cl.[7] .................. C07K 16/00; C07K 14/00; G01N 33/53
(52) U.S. Cl. .................. 530/387.9; 530/388.1; 530/389.1; 530/350; 435/7.1
(58) Field of Search ............ 530/388.1, 389.1, 530/350, 387.9; 435/7.1

(56) References Cited

PUBLICATIONS

Zou et al. Proc. Nat. Acad. Sci. 2000, vol. 97, pp. 13726–13731.*
Hamm J. Biol. Chem., 1998, vol. 278, pp. 669–672.*
IMAGE consortium, Accession No. AA250332, Mar. 12, 1997.*
Lin et al., Extended Life–Span and Stress Resistance in the Drosophila Mutant methuselah. Science 1998, vol. 282, pp. 943–946.*
Arking et al., Elevated Paraquat Resistance Can Be Used as a Bioassay for Longevity in a Genetically Based Long–Lived Strain of Drosophila Dev Genet 1991 vol 12 pp. 362–370.*

* cited by examiner

Primary Examiner—Lorraine Spector
Assistant Examiner—Janet L. Andres
(74) Attorney, Agent, or Firm—Fish & Richardson P.C.

(57) ABSTRACT

Disclosed are polypeptides and polynucleotides having stress and life span modulating activity. The polypeptides and polynucleotides are useful in identifying and modulating stress-associated disorders.

16 Claims, 11 Drawing Sheets

| | | |
|---|---|---|
| MTH   | NCLIVPSITGQTVVMISLICMVLTIAVYLFVKKLQNLHGKCFICYMVCL | 257 |
| hCD97 | NELLLSVIT--WVGIVISLFCLILCILTELLVRPIQGSRTTIHLCICL | 497 |
| rLR   | VISIVCLAICISTFCFLRGLQTDRNTIHKNLCINL              | 902 |
| mEMR-1| VISIVCLAIATELLCRAVQNHNTYMHLCVCL                  | 690 |
|       | SL.C.          I.         .        Q.    ..L     |     |

| | | |
|---|---|---|
| MTH   | FMGYLFLILDIWQISISF----CKPAGFIGYFVMAAFWLSVISIHIWNT | 304 |
| hCD97 | FVGSTIFLAGIENEGGQVGLRCRIVAGILHYCFLAAFCWMSIEGIELYFL | 547 |
| rLR   | FLAELIFLVGIDKTQYEV--ACPIFAGILHYFELAAFSWLCLEGVHLYLL | 950 |
| mEMR-1| FLAKILFLTGIDKTDNQT--ACAIIAGFLHYLFLACFWMLVEAVMFLM   | 738 |
|       | F.   L                   . A.F.W...   .  L        |     |

| | | |
|---|---|---|
| MTH   | FRGSSHKANRLFEHR----FLAYNTYAWGMAVVLTGITVLADNIVENQDW | 351 |
| hCD97 | VVRVFQGQ---GLSTR------------WLCLIGYGVPLIIVGVSAAIY  | 581 |
| rLR   | LVEVFESE---YSRTK------------YYYLGGYCFPALVVGIAAAID  | 984 |
| mEMR-1| VRNLKVVN---YFSSRNIKMLHLCAFGYGLPVLVVIISASVQ         | 777 |
|       |                            .  . A..F.W... .       |     |

| | | |
|---|---|---|
| MTH   | NPR--VGHEGHCWIYTQAWSAMLYFYGPMVFLIAEFNITMFLLTAKRILGVK | 400 |
| hCD97 | -SKGYGRPRYCWLDFEEQG-FLWSFLGPVTFIILQNAVIFVTTVWKLTQKF  | 629 |
| rLR   | -YRSYGTEKACWLRVDNY-FIWSFIGPVSFIVVNLVFIMVTLHKMIRSS    | 1032|
| mEMR-1| -PRGYGMHNRCWLNTETG-FIWSFLGPVCMIITINSVLLAWTLWVLRQKL   | 825 |
|       |    G.  CW.         F GP.  .I.  N       T       ..   |     |

*FIG. 4A*

```
MTH    KDIQNFAHRQERKQKLNSDKQTYFFIRLFIIMGLSWSLEIGSYFSQSNQ  450
hCD97  SEIN----------PDMKKLKKARAITITATAQLFLL-GCTWVEGIFIFDDRS-  671
rLR    SVLK----------PDSSRIDNIKSWALGAIALFLL-GLTWAFGILFINKES-  1074
mEMR-1 CSVS----------SEVSKIKDTRLIIFKAIAQIFIL-GCSWVLGIFQIGPLA  867
                      .         . LF.L G .W             S

MTH    TWANVFLVADYLNWSQGIIFIIFVL
hCD97  ---LVLTYVFTILNCLQGAFLYLIHCL
rLR    ---VVMAYLFTTFNAFQGVFIFV
mEMR-1 ---SIMAYLFTIINSLQGAFIFLIHCL
          .  N       QG            L
```

FIG. 4B

METHUSELAH GENE, COMPOSITIONS AND METHODS OF USE

CROSS REFERENCE TO RELATED APPLICATIONS

This application is a divisional of application Ser. No. 09/370,098, filed Aug. 6, 1999, now U.S. Pat. No. 6,303,768, which claims priority from Provisional Application Ser. No. 60/095,826, filed Aug. 7, 1998, to which application a priority claim is made under 35 U.S.C. '119(e). Each application is incorporated herein by reference in its entirety.

The U.S. Government has certain rights in this invention pursuant to Grant Nos. EY09278 and AG12289 awarded by the National Institute of Health, and Grant No. MCB9408718 awarded by the National Science Foundation.

FIELD OF THE INVENTION

This invention relates to newly identified polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been identified as a G-protein-coupled receptors having stress associated and life span associated activities.

BACKGROUND OF THE INVENTION

Studies on the genetics of aging in a number of organisms including the yeast *Saccharomyces cerevisiae,* the roundworm *Caenorhabditis elegans,* and the fruit fly *Drosophila melanogaster* have revealed the role of metabolic capacity and resistance to stress in determining life span. One mode of modulation of longevity has been suggested to be signal transduction. Signal transduction has emerged as an important molecular mechanism underlying longevity. The results obtained from the study of these organisms are applicable to the dietary restriction paradigm in mammals. It is thought that many of the molecular characteristics identified from these studies will be of interest in determining the effect of diet and signal transduction in the life span of mammals. However, the identification and role of the genes and gene products responsible for modulating the life-span of organism are not yet fully understood. Accordingly, there is a desire to obtain and characterize life-span modulating genes in order to more fully understand the role of stress and life-span.

The effect of genes on life span in *Drosophila* has been established by selective breeding (Rose et al. Genetics, 97, 173–186 (1981)). However, that methodology involves the participation of multiple genes with additive and quantitative effects that can be difficult to unravel. A more incisive approach is to use single gene mutations. A search for life-extension mutants can lead to the identification of individual genes that regulate biological aging.

SUMMARY OF THE INVENTION

In a first embodiment, the present invention provides a substantially purified Methuselah (MTH) polypeptide having an amino acid sequence as set forth in SEQ ID NO:2.

In another embodiment, the present invention provides an isolated polynucleotide encoding an amino acid sequence as set forth in SEQ ID NO:2. The isolated polynucleotide is selected from the group consisting of SEQ ID NO:1; SEQ ID NO:1, wherein T can also be U; a nucleic acid sequence complementary to SEQ ID NO:1; and fragments of a), b), or c) that are at least 15 bases in length and that hybridize under stringent conditions to DNA which encodes the polypeptide of SEQ ID NO:2.

In another embodiment, the present invention provides an expression vector containing an mth polynucleotide. The vector can be for example, a plasmid or a viral vector.

In yet another embodiment, the present invention provides a host cell transformed with an expression vector containing an mth polynucleotide.

In yet a further embodiment, the present invention provides a method of producing an MTH polypeptide by transforming a host cell with an mth polynucleotide; expressing the polynucleotide in the host; and recovering the MTH polypeptide.

In another embodiment, an antibody that binds to the polypeptide of SEQ ID NO:2 is provided. The antibody can be polyclonal or monoclonal.

The present invention also provides a method for identifying a compound which modulates mth expression or activity comprising: incubating components comprising the compound and an MTH polypeptide, or a recombinant cell expressing an MTH polypeptide, under conditions sufficient to allow the components to interact; and determining the effect of the compound on the expression or activity of the gene or polypeptide, respectively.

In yet another embodiment, the present invention provides a method of detecting an mth-specific cell component in a sample comprising: contacting a sample suspected of containing mth with a reagent that binds to the mth-specific component; and detecting binding of the reagent to the component.

In yet a further embodiment, the present invention provides a method of promoting insect cell survival in vitro comprising contacting the cell with a survival promoting amount of a compound containing an MTH polypeptide or a agent capable of modulating MTH activity or expression.

In yet another embodiment, the present invention provides a method of producing a non-human organism having an increased life span comprising: introducing a transgene disrupting or interfering with expression of Methuselah (mth) into germ cells of a pronuclear embryo of the organism; implanting the embryo into the oviduct of a pseudopregnant female thereby allowing the embryo to mature to full term progeny; testing the progeny for presence of the transgene to identify transgene-positive progeny; and cross-breeding transgene-positive progeny to obtain further transgene-positive progeny.

In yet another embodiment, the present invention provides a transgenic organims having a phenotype characterized by an increase in mass or an increase in life span or an increase in resistance to a biologic stress. The organism may be any non-human organsims, including, for example, bovine, porcine and invetebrates, such as *Drosophila*.

In another embodiment, the present invention provides a method of increasing the life span of a subject, comprising: administering to the subject, a reagent which affects mth activity or expression.

In yet a further embodiment, the present invention provides a kit useful for the detection of an MTH polypeptide, the kit comprising a carrier containing one or more containers comprising a first container containing a mth binding reagent. These and other aspects of the present invention will be apparent to those of skill in the art from the teachings herein.

BRIEF DESCRIPTION OF THE DRAWINGS

The following drawings and figures are illustrative of embodiments of the invention and are not meant to limit the scope of the invention as encompassed by the claims.

Distilled water was added to keep the filters moist during the test. C. Thermal stress test. Flies (age five days) were transferred to vials containing 1% agar in 5% sucrose solution, and maintained at 36° C. Initially, immobilized flies were scored every 30 minutes; as immobilization accelerated, scoring was done every 5 minutes.

FIG. 3 shows the mth gene. The full-length cDNA and its corresponding genomic segment are shown. A. The genomic DNA. The letters represent restriction enzyme sites; E, EcoR I; P, Pst I; Sa, Sac I; Sm, Sma I; X, Xba I. Boxes indicate exons; hatched boxes the open reading frame. The P-element insertion site is indicated by an arrow. The two plasmid rescue clones, 44P1 and 44E1 represent, respectively, upstream and downstream fragments relative to the P-element. The structure is based on the genomic sequence derived from the P1 plasmid, DS06692 of the BDGP. B. cDNA and protein sequence. Nucleotides are in plain letters, amino acids in italics; numbers of the nucleotide and amino acid sequence are indicated to the left and right, respectively. The putative leader peptide sequence is in bold face; transmembrane domains are underlined. The polyadenylation site is boxed. The sequence is derived from LD08316 of the BDGP. C. Hydropathic profile of the MTH protein, analyzed by the Kyte-Doolittle algorithm. The seven hydrophobic regions (excluding the N-terminal putative leader peptide) are designated.

FIG. 4 shows the alignment of MTH with several known G-protein coupled receptors. The predicted MTH protein is aligned to partial sequences of the human leukocyte surface antigen CD97 (hCD97, GenBank accession number P48960, SEQ ID NO:3), rat α-latrotoxin receptor (rLR, U72487, SEQ ID NO:4), and mouse EGF-module-containing receptor (mEMR-1, Q61549, SEQ ID NO:5). Dark shading indicates identity, gray shading similarity. The seven transmembrane domains of MTH are indicated by lines above each row. Consensus amino acids are. cited below; similar residues are indicated by dots.

Figure 5:
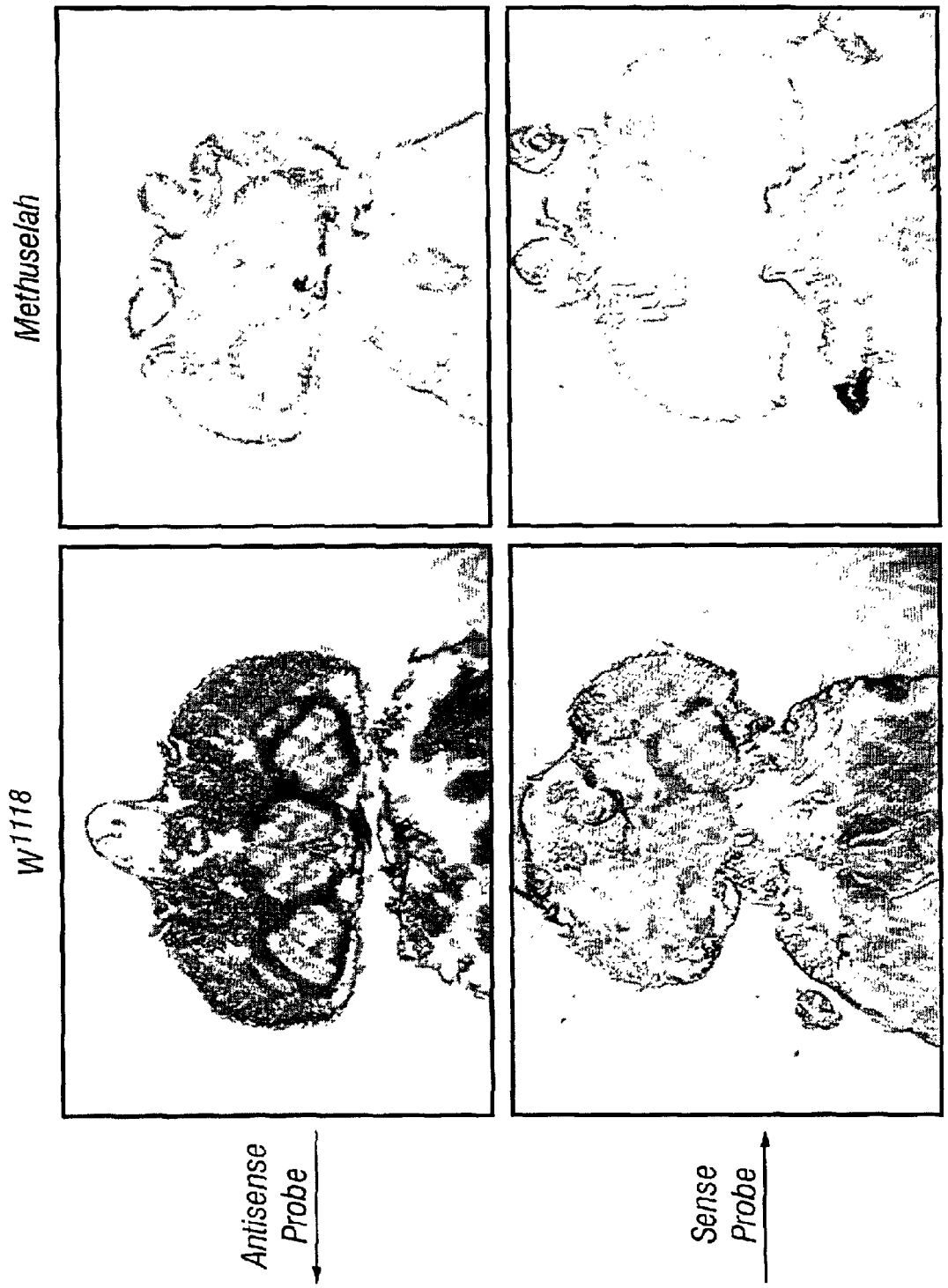

FIG. 5 shows the expression in wild type (e.g., w[1118]) flies compared to mth mutant flies (P+/mth+) in the head region of *Drosophila* flies. The expression of mth was reduced to about 10%.

Figure 6:
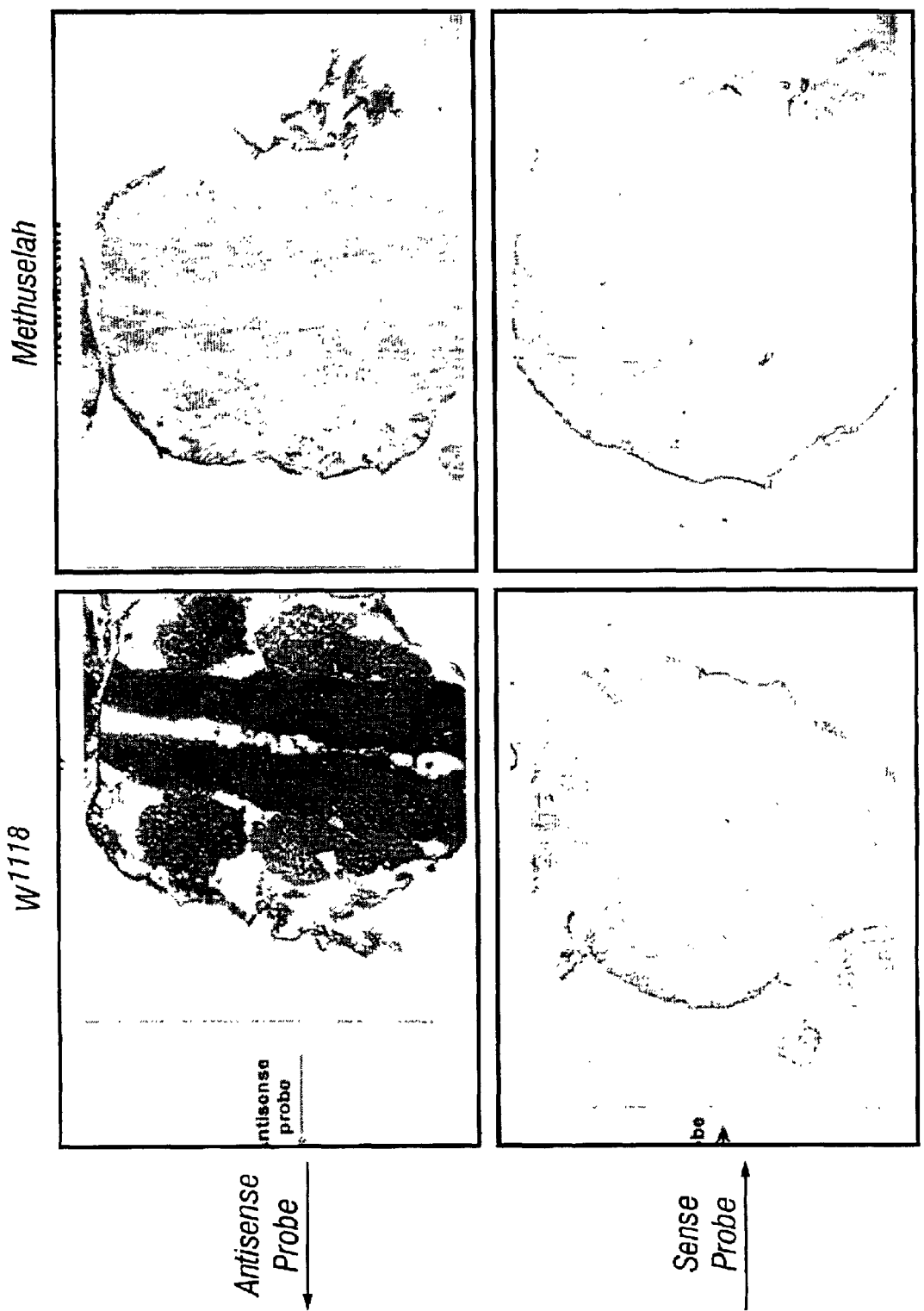

FIG. 6 shows the expression of mth in wild type flies compared to mth flies (P+/mth+) in the thoracic region of the fly.

Figure 7:
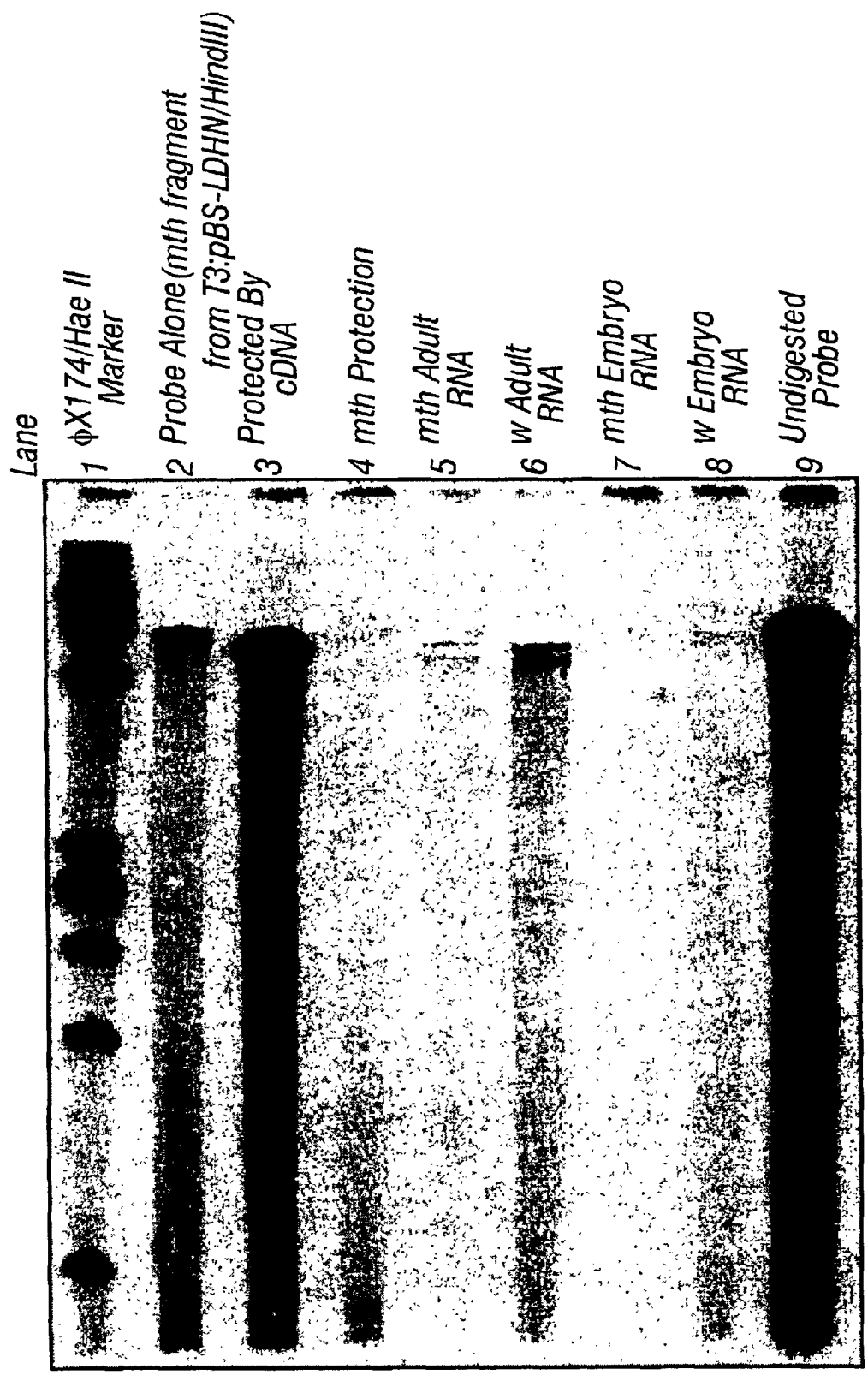
Figure 8A:
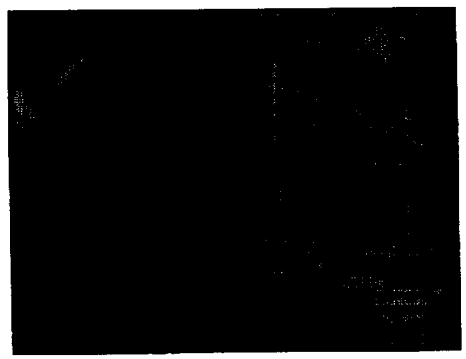
Figure 8B:
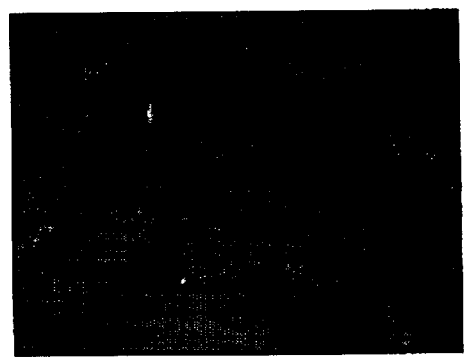
Figure 8C:
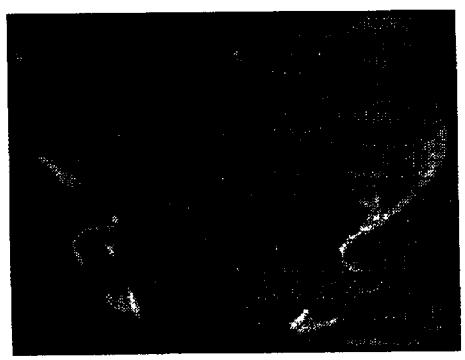
Figure 8D:
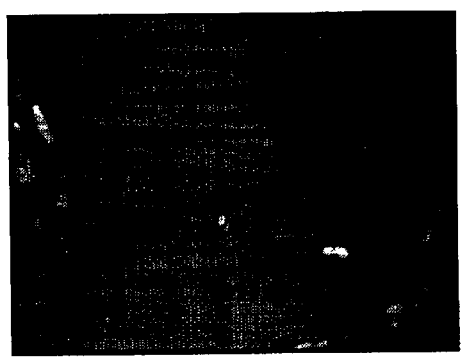
Figure 8E:
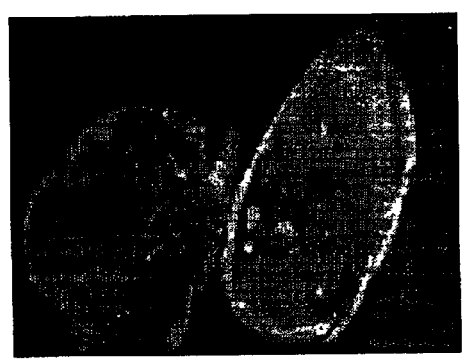
Figure 8F:
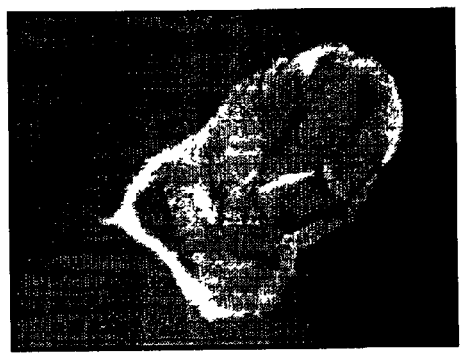
Figure 8G:
Figure 8H:
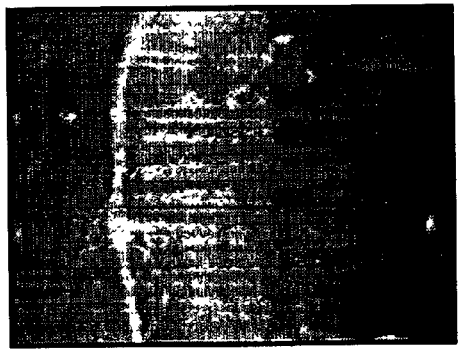

FIG. 7 shows a gel from an RNAse protection assay comparing the expression of mth in wildtype flies and mth mutant flies (P+/mth+). Lane 5 represents RNA from mth adult flies, demonstrating a reduction in expression of mth in P+/mth+ *Drosophila* compared to lane 6. Lane 6 shows RNA from wildtype *Drosophila* (mth+/mth+). Lane 7 and 8 demonstrate the difference in expression of mth in mutant flies (lane 7) compared to wildtype (lane 8) in *Drosophila* embryos.

FIG. 8 shows the localization and expression of mth in *Drosophila* mth mutants and wildtype flies using a monoclonal antibody to mth and developed with an anti-mouse secondary antibody and FITC. The left series of panels represents wildtype flies (i.e., panels A, C, E, and G) and the right series of panels represents the mth mutant flies (i.e., panels B, D, F, and H). Panels A–B are from the trunk thoracic muscles of the flies. Panels C–D are from the ventral layer of the thoracic region. Panels E–F are from leg muscles of the flies. Panels G–H are from the proboscis muscles of the flies.

DETAILED DESCRIPTION OF THE INVENTION

The present invention provides polypeptides and polynucleotides encoding the polypeptides, wherein each polypeptide is characterized as a stress related or life span modulating polypeptide termed, herein, a Methuselah polypeptide.

The present invention originated from the discovery and cloning of a stress related gene termed Methuselah (mth), which encode a polypeptide (MTH) identified from invertebrates (e.g., *Drosophila*). This gene, referred to as mth, encodes a polypeptide which affects life span and susceptibility to biological stress factors. The demonstration of life span enhancing and stress resistance activity of the *Drosophila* mth family member raises the possibility that a mammalian family member may have similar functions, and that altering the activity (i.e., enhancing or reducing) may be important in promoting the life span of cells and subjects as well as promoting resistance to biological stress.

To facilitate understanding of the invention, a number of terms are defined below.

The term "isolated" means altered "by the hand of man" from its natural state; i.e., if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein.

As part of or following isolation, a polynucleotide can be joined to other polynucleotides, such as for example DNAs, for mutagenesis studies, to form fusion proteins, and for propagation or expression of the polynucleotide in a host. The isolated polynucleotides, alone or joined to other polynucleotides, such as vectors, can be introduced into host cells, in culture or in whole organisms. Such polynucleotides, when introduced into host cells in culture or in whole organisms, still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions which are not naturally occurring compositions) and, therein remain isolated polynucleotides or polypeptides within the meaning of that term as it is employed herein.

The term "ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989).

The term "oligonucleotide" as used herein is defined as a molecule comprised of two or more deoxyribonucleotides or ribonucleotides, preferably more than three, and usually more than ten. The exact size of an oligonucleotide will depend on many factors, including the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, Meth. Enzymol., 68:90–99; the phosphodiester method of Brown et al., 1979, Method Enzymol., 68:109–151, the diethylphosphoramidite method of Beaucage et al., 1981, Tetrahedron Lett., 22:1859–1862; the triester method of Matteucci et al., 1981, J. Am. Chem. Soc., 103:3185–3191, or automated synthesis methods; and the solid support method of U.S. Pat. No. 4,458,066.

The term "plasmids" generally is designated herein by a lower case p preceded and/or followed by capital letters and/or numbers, in accordance with standard naming conventions that are familiar to those of skill in the art.

Plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

"Polynucleotide" or "nucleic acid sequence" refers to a polymeric form of nucleotides at least 10 bases in length. By "isolated nucleic acid sequence" is meant a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double stranded forms of DNA.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

Nucleic acid sequences which encode a fusion protein of the invention can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., *Methods in Enzymology* 153:516–544, 1987). For example, when cloning in bacterial systems, inducible promoters such as pL of bacteriophage γ, plac, ptrp, ptac (ptrp-lac hybrid promoter)

and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the nucleic acid sequences encoding a fusion protein of the invention may be inserted into a recombinant expression vector. The term "recombinant expression vector" refers to a plasmid, virus or other vehicle known in the art that has been manipulated by insertion or incorporation of the nucleic acid sequences encoding the fusion peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem.* 263:3521, 1988), baculovirus-derived vectors for expression in insect cells, cauliflower mosaic virus, CaMV; tobacco mosaic virus, TMV. The nucleic acid sequences encoding a fusion polypeptide of the invention can also include a localization sequence to direct the indicator to particular cellular sites by fusion to appropriate organellar targeting signals or localized host proteins. A polynucleotide encoding a localization sequence, or signal sequence, can be used as a repressor and thus can be ligated or fused at the 5' terminus of a polynucleotide encoding the reporter polypeptide such that the signal peptide is located at the amino terminal end of the resulting fusion polynucleotide/polypeptide. The construction of expression vectors and the expression of genes in transfected cells involves the use of molecular cloning techniques also well known in the art. Sambrook et al., *Molecular Cloning—A Laboratory Manual,* Cold Spring Harbor Laboratory, Cold Spring Harbor, N.Y., 1989, and *Current Protocols in Molecular Biology,* M. Ausubel et al., eds., (Current Protocols, a joint venture between Greene Publishing Associates, Inc. and John Wiley & Sons, Inc., most recent Supplement). These methods include in vitro recombinant DNA techniques, synthetic techniques and in vivo recombination/genetic recombination. (See, for example, the techniques described in Maniatis, et al., *Molecular Cloning A Laboratory Manual,* Cold Spring Harbor Laboratory, N.Y., 1989).

Depending on the vector utilized, any of a number of suitable transcription and translation elements, including constitutive and inducible promoters, transcription enhancer elements, transcription terminators, etc. may be used in the expression vector (see, e.g., Bitter, et al., *Methods in Enzymology* 153:516–544, 1987). These elements are well known to one of skill in the art.

In yeast, a number of vectors containing constitutive or inducible promoters may be used. For a review see, *Current Protocols in Molecular Biology,* Vol. 2, Ed. Ausubel, et al., Greene Publish. Assoc. & Wiley Interscience, Ch. 13, 1988; Grant, et al., "Expression and Secretion Vectors for Yeast," in *Methods in Enzymology,* Eds. Wu & Grossman, 1987, Acad. Press, New York, Vol. 153, pp.516–544, 1987; Glover, *DNA Cloning,* Vol. II, IRL Press, Wash., D.C., Ch. 3, 1986; and Bitter, "Heterologous Gene Expression in Yeast," *Methods in Enzymology,* Eds. Berger & Kimmel, Acad. Press, New York, Vol. 152, pp. 673–684, 1987; and *The Molecular Biology of the Yeast Saccharomyces,* Eds. Strathern et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: *DNA Cloning Vol.* 11, *A Practical Approach,* Ed. DM Glover, IRL Press, Wash., D.C., 1986). Alternatively, vectors may be used which promote integration of foreign DNA sequences into the yeast chromosome.

An alternative expression system which could be used to express the proteins of the invention is an insect system. In one such system, *Autographa californica* nuclear polyhedrosis virus (AcNPV) is used as a vector to express foreign genes. The virus grows in *Spodoptera frugiperda* cells. The sequence encoding a protein of the invention may be cloned into non-essential regions (for example, the polyhedrin gene) of the virus and placed under control of an AcNPV promoter (for example the polyhedrin promoter). Successful insertion of the sequences coding for a protein of the invention will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., *J. Viol.* 46:584, 1983; Smith, U.S. Pat. No. 4,215,051.

By "transformation" is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

By "transformed cell" or "host cell" is meant a cell (e.g., prokaryotic or eukaryotic) into which (or into an ancestor of which) has been introduced, by means of recombinant DNA techniques, a DNA molecule encoding a polypeptide of the invention (i.e., a Methuselah polypeptide), or fragment thereof.

Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding a polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors,* Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*), or may be a mammalian cell, including a human cell.

Eukaryotic systems, and mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used. Such host cell lines may include but are not limited to CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, the nucleic acid sequences encoding a fusion protein of the invention may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the Methuselah polypeptide in infected hosts (e.g., see Logan & Shenk, *Proc. Natl. Acad. Sci. USA* 81:3655–3659, 1984). Alternatively, the vaccinia virus 7.5K promoter may be used. (e.g., see, Mackett, et al., *Proc. Natl. Acad. Sci. USA*, 79:7415–7419, 1982; Mackett, et al., *J. Virol* 49:857–864, 1984; Panicali, et al., *Proc. Natl. Acad. Sci. USA* 79:4927–4931, 1982). Of particular interest are vectors based on bovine papilloma virus which have the ability to replicate as extrachromosomal elements (Sarver, et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the Methuselah gene in host cells (Cone & Mulligan, *Proc. Natl. Acad. Sci. USA* 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the cDNA encoding a fusion protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell*, 11:223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell*, 22:817, 1980) genes can be employed in tk$^-$, hgprt$^-$ or aprt$^-$ cells respectively. Also, antimetabolite resistance can be used as the basis of selection for dhfr, which confers resistance to methotrexate (Wigler, et al., *Proc. Natl. Acad. Sci. USA* 77:3567, 1980; O'Hare, et al., *Proc. Natl. Acad. Sci. USA* 8:1527, 1981); gpt, which confers resistance to mycophenolic acid (Mulligan & Berg, *Proc. Natl. Acad. Sci. USA*, 78:2072, 1981; neo, which confers resistance to the aminoglycoside G-418 (Colberre-Garapin, et al., *J. Mol. Biol.* 150:1, 1981); and hygro, which confers resistance to hygromycin (Santerre, et al., *Gene* 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047, 1988); and ODC (ornithine decarboxylase) which confers resistance to the ornithine decarboxylase inhibitor, 2-(difluoromethyl)-DL-ornithine, DFMO (McConlogue L., In: *Current Communications in Molecular Biology*, Cold Spring Harbor Laboratory, ed., 1987).

The term "primer" as used herein refers to an oligonucleotide, whether natural or synthetic, which is capable of acting as a point of initiation of synthesis when placed under conditions in which primer extension is initiated or possible. Synthesis of a primer extension product which is complementary to a nucleic acid strand is initiated in the presence of nucleoside triphosphates and a polymerase in an appropriate buffer at a suitable temperature.

The term "primer" may refer to more than one primer, particularly in the case where there is some ambiguity in the information regarding one or both ends of the target region to be synthesized. For instance, if a nucleic acid sequence is inferred from a protein sequence, a "primer" generated to synthesize nucleic acid encoding said protein sequence is actually a collection of primer oligonucleotides containing sequences representing all possible codon variations based on the degeneracy of the genetic code. One or more of the primers in this collection will be homologous with the end of the target sequence. Likewise, if a "conserved" region shows significant levels of polymorphism in a population, mixtures of primers can be prepared that will amplify adjacent sequences. For example, primers can be synthesized based upon the amino acid sequence as set forth in SEQ ID NO:2 and can be designed based upon the degeneracy of the genetic code.

The term "restriction endonucleases" and "restriction enzymes" refers to bacterial enzymes which cut double-stranded DNA at or near a specific nucleotide sequence.

The term "gene" means the segment of DNA involved in producing a polypeptide chain; it includes regions preceding and following the coding region (leader and trailer) as well as intervening sequences (introns) between individual coding segments (exons).

A coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

A "recombinant" protein or polypeptide refer to proteins or polypeptides produced by recombinant DNA techniques; i.e., produced from cells transformed by an exogenous DNA construct encoding the desired polypeptide (e.g. a Methuselah polypeptide of the present invention). "Synthetic" polypeptides are those prepared by chemical synthesis.

As used in connection with the present invention the term "polypeptide" or "protein" refers to a polymer in which the monomers are amino acid residues which are joined together through amide bonds. When the amino acids are alpha-amino acids, either the L-optical isomer or the D-optical isomer can be used, the L-isomers being preferred. The term "polypeptide" as used herein is intended to encompass any amino acid sequence and include modified sequences such as glycoproteins. The term "polypeptide" is specifically intended to cover naturally occurring proteins, as well as those which are recombinantly or synthetically synthesized, which occur in at least two different conformations wherein both conformations have the same or substantially the same amino acid sequence but have different three dimensional structures. "Fragments" are a portion of a naturally occurring protein. Fragments can have the same or substantially the same amino acid sequence as the naturally occurring protein. "Substantially the same" means that an amino acid sequence is largely, but not entirely, the same, but retains a functional activity of the sequence to which it is related. In general, two amino acid sequences are "substantially the same" or "substantially homologous" if they are at least 85% identical. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide. Examples of conservative substitutions involve amino acids that have the same or similar properties. Illustrative amino acid conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation, for example of possible modifications. The modified peptides can be chemically synthesized, or the isolated gene can be site-directed mutagenized, or a synthetic gene can be synthesized and expressed in bacteria, yeast, baculovirus, tissue culture and so on.

A DNA "coding sequence of" or a "nucleotide sequence encoding" a particular protein, is a DNA sequence which is transcribed and translated into an protein when placed under the control of appropriate regulatory sequences.

MTH Nucleic Acid, Polypeptides and Method of Expression

In one embodiment, the invention provides an isolated polynucleotide sequence encoding MTH polypeptide. An exemplary MTH polypeptide of the invention has an amino acid sequence as set forth in SEQ ID NO:2. Polynucleotide sequences of the invention include DNA, cDNA and RNA sequences which encode MTH. It is understood that all polynucleotides encoding all or a portion of MTH are also included herein, so long as they encode a polypeptide with MTH activity (e.g., increased life span or resistance to stress). Such polynucleotides include naturally occurring, synthetic, and intentionally manipulated polynucleotides. For example, MTH polynucleotide may be subjected to site-directed mutagenesis. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of MTH polypeptide encoded by the nucleotide sequence is functionally unchanged. Also included are nucleotide sequences which encode MTH polypeptide, such as SEQ ID NO:1. In addition, the invention also includes a polynucleotide encoding a polypeptide having the biological activity of an amino acid sequence of SEQ ID NO:2 and having at least one epitope for an antibody immunoreactive with MTH polypeptide. However, it is recognized that portions of either SEQ ID NO:1 or 2 may be excluded to identify fragments of the polynucleotide sequence or polypeptide sequence. For example, fragments of SEQ ID NO:1 or 2 are encompassed by the current invention, so long as they retain some biological activity related to mth. A biological activity related to MTH includes for example, antigencity or the ability to affect stress and life span in an organism.

The polynucleotides of this invention were originally recovered from *Drosophila melanogaster*. Thus, the present invention provides means for isolating the nucleic acid molecules from other organisms, including humans, encoding the polypeptides of the present invention. For example, one may probe a gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated by one skilled in the art that probes can be designed based on the degeneracy of the genetic code to the sequences set forth in SEQ ID NO:2.

The invention includes polypeptides having substantially the same sequence as the amino acid sequence set forth in SEQ ID NO:2 or functional fragments thereof, or amino acid sequences that are substantially identical or the same as SEQ ID NO:2.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol* 48:443 (1970), by the search for similarity method of person & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

On example of a useful algorithm is BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) or 11, an expectation (E) or 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Natl. Acad. Sci. USA* 90:5873 (1993)). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

A "substantially pure polypeptide" is an MTH polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, MTH polypeptide. A substantially pure MTH polypeptide may be obtained, for example, by extraction from a natural source (e.g., an insect cell); by expression of a recombinant nucleic acid encoding an MTH polypeptide; or by chemically synthesizing the protein. Purity can be measured by any appropriate method, e.g., by column chromatography, polyacrylamide gel electrophoresis, or by HPLC analysis.

MTH polypeptides of the present invention include peptides, or full length protein, that contains substitutions, deletions, or insertions into the protein backbone, that would still leave an approximately 50%–70% homology to the original protein over the corresponding portion. A yet greater degree of departure from homology is allowed if like-amino acids, i.e. conservative amino acid substitutions, do not count as a change in the sequence.

In addition to polypeptides of the invention, specifically disclosed herein is a DNA sequence for MTH represented by SEQ ID NO:1. DNA sequences of the invention can be obtained by several methods. For example, the DNA can be isolated using hybridization or computer-based techniques which are well known in the art. These include, but are not limited to: 1) hybridization of genomic libraries with probes to detect homologous nucleotide sequences; 2) antibody screening of expression libraries to detect cloned DNA fragments with shared structural features; 3) polymerase chain reaction (PCR) on genomic DNA using primers capable of annealing to the DNA sequence of interest; and 4) computer searches of sequence databases for similar sequences.

The polynucleotide encoding MTH includes the nucleotide sequence in FIG. 3 (SEQ ID NO:1), as well as nucleic acid sequences complementary to that sequence. When the sequence is RNA, the deoxyribonucleotides A, G, C, and T of SEQ ID NO:1 are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes the protein of FIG. 3 (e.g., SEQ ID NO:2). "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, New York, incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Oligonucleotides encompassed by the present invention are also useful as primers for nucleic acid amplification reactions. In general, the primers used according to the method of the invention embrace oligonucleotides of sufficient length and appropriate sequence which provides specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15–22 or more nucleotides, although it may contain fewer nucleotides as long as the primer is of sufficient specificity to allow essentially only the amplification of the specifically desired target nucleotide sequence (i.e., the primer is substantially complementary).

Amplified products may be detected by Southern blot analysis, without using radioactive probes. In such a process, for example, a small sample of DNA containing a very low level of MTH nucleotide sequence is amplified and analyzed via a Southern blotting technique known to those of skill in the art. The use of non-radioactive probes or labels is facilitated by the high level of the amplified signal.

MTH polynucleotide of the invention is derived from an insect (e.g., *Drosophila*). Screening procedures which rely on nucleic acid hybridization make it possible to isolate any gene sequence from any organism, provided the appropriate probe is available. For example, it is envisioned that such probes can be used to identify other homologs of the mth family of factors in insects or, alternatively, in other organisms such as mammals, e.g., humans. In accomplishing this, oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of DNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.,* 9:879, 1981).

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned.

DNA sequences encoding MTH can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used.

In the present invention, the MTH polynucleotide sequences may be inserted into a recombinant expression vector. The term "recombinant expression vector" refers to a plasmid, virus or other vehicle known in the art that has been manipulated by insertion or incorporation of the MTH genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include those described above.

Polynucleotide sequences encoding MTH can be expressed in either prokaryotes or eukaryotes. Hosts can include microbial, yeast, insect and mammalian organisms. Such vectors are used to incorporate DNA sequences of the invention.

Methods which are well known to those skilled in the art can be used to construct expression vectors containing the MTH coding sequence and appropriate transcriptional/translational control signals. These methods include in vitro recombinant DNA techniques, synthetic techniques, and in vivo recombination/genetic techniques. (See, for example, the techniques described in Maniatis et al., 1989, *Molecular Cloning A Laboratory Manual,* Cold Spring Harbor Laboratory, New York)

The genetic construct can be designed to provide additional benefits, such as, for example addition of C-terminal or N-terminal amino acid residues that would facilitate purification by trapping on columns or by use of antibodies. All those methodologies are cumulative. For example, a synthetic gene can later be mutagenized. The choice as to the method of producing a particular construct can easily be made by one skilled in the art based on practical considerations: size of the desired peptide, availability and cost of starting materials, etc. All the technologies involved are well established and well known in the art. See, for example, Ausubel et al., *Current Protocols in Molecular Biology,* Volumes 1 and 2 (1987), with supplements, and Maniatis et al., *Molecular Cloning, a Laboratory Manual,* Cold Spring Harbor Laboratory (1989). Yet other technical references are known and easily accessible to one skilled in the art.

Antibodies that Bind to MTH

In another embodiment, the present invention provides antibodies that bind to MTH. Such antibodies are useful for research and diagnostic tools in the study of biological stress and life span, and associated pathologies in general. Such antibodies may be administered alone or contained in a pharmaceutical composition comprising antibodies against MTH and other reagents effective as modulators of biological stress and life span both in vitro and in vivo.

The term "epitope", as used herein, refers to an antigenic determinant on an antigen, such as a MTH polypeptide, to which the paratope of an antibody, such as an MTH-specific antibody, binds. Antigenic determinants usually consist of chemically active surface groupings of molecules, such as amino acids or sugar side chains, and can have specific three-dimensional structural characteristics, as well as specific charge characteristics.

Antibodies which bind to the MTH polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

An antibody suitable for binding to MTH is specific for at least one portion of an extracellular region of the MTH polypeptide, as shown in FIG. 3 (SEQ ID NO:2). For example, one of skill in the art can use the peptides to generate appropriate antibodies of the invention. Antibodies of the invention include polyclonal antibodies, monoclonal antibodies, and fragments of polyclonal and monoclonal antibodies.

The preparation of polyclonal antibodies is well-known to those skilled in the art. See, for example, Green et al., *Production of Polyclonal Antisera*, in *Immunochemical Protocols* (Manson, ed.), pages 1–5 (Humana Press 1992); Coligan et al., *Production of Polyclonal Antisera in Rabbits, Rats, Mice and Hamsters*, in *Current Protocols in Immunology*, section 2.4.1 (1992), which are hereby incorporated by reference.

The preparation of monoclonal antibodies likewise is conventional. See, for example, Kohler & Milstein, *Nature*, 256:495 (1975); Coligan et al., sections 2.5.1–2.6.7; and Harlow et al., *Antibodies: A Laboratory Manual*, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., *Purification of Immunoglobulin G (IgG)*, in *Methods in Molecular Biology*, Vol. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., *Int. J. Cancer*, 46:310 (1990), which are hereby incorporated by reference.

Alternatively, a therapeutically useful anti-MTH antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA*, 86:3833 (1989), which is hereby incorporated in its entirety by reference. Techniques for producing humanized monoclonal antibodies are described, for example, by Jones et al., *Nature*, 321: 522 (1986); Riechmann et al., *Nature*, 332: 323 (1988); Verhoeyen et al., *Science*, 239:1534 (1988); Carter et al., *Proc. Nat'l Acad. Sci. USA*, 89:4285 (1992); Sandhu, *Crit. Rev. Biotech.*, 12:437 (1992); and Singer et al., *J. Immunol.*, 150:2844 (1993), which are hereby incorporated by reference.

Antibodies of the invention also may be derived from human antibody fragments isolated from a combinatorial immunoglobulin library. See, for example, Barbas et al., *Methods: A Companion to Methods in Enzymology*, Vol. 2, page 119 (1991); Winter et al., *Ann. Rev. Immunol.* 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.*, 7:13 (1994); Lonberg et al., *Nature*, 368:856 (1994); and Taylor et al., *Int. Immunol.*, 6:579 (1994), which are hereby incorporated by reference.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisonhoff et al., *Arch. Biochem. Biophys,.* 89:230 (1960); Porter, *Biochem. J.*, 73:119 (1959); Edelman et al., *Methods in Enzymology*, Vol. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA*, 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., Methods: A Companion to *Methods in Enzymology*, Vol. 2, page 97 (1991); Bird et al., *Science*, 242:423 (1988); Ladner et al., U.S. Pat. No. 4,946,778; Pack et al., *Bio/Technology*, 11:1271 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology*, Vol. 2, page 106 (1991).

When used for immunotherapy, the monoclonal antibodies, fragments thereof, or both, of the invention that bind to mth may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science*, 231:148, 1986) and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The labeled or unlabeled monoclonal antibodies of the invention can also be used in combination with therapeutic agents such as those described above. Especially preferred are therapeutic combinations comprising the monoclonal antibody of the invention and immunomodulators and other biological response modifiers.

The dosage ranges for the administration of monoclonal antibodies of the invention are those large enough to produce the desired effect (e.g., a change in susceptibility to stress or life span). The dosage should not be so large as to cause adverse side effects, such as unwanted cross-reactions, anaphylactic reactions, and the like. Generally, the dosage will vary with the age, condition, sex and extent of an mth-associated disorder or the desired change in the subject and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

Modulation of Biological Stress or Life Span

In one embodiment, the invention provides a method for modulating (e.g., reducing) the effect of biological stress in a cell or a subject by administering to the cell or subject a therapeutically effective amount of a composition which contains an MTH polypeptide, or biologically functional fragment thereof or an agent (e.g., an antibody, ribozyme, antisense molecule, or double-stranded interferring RNA molecules). The term "biologically functional fragment" encompasses any segment of a MTH polypeptide that retains the ability to modulate (e.g., increase or decrease) biological stress and/or life span.

As used herein, a "therapeutically effective amount" of a composition containing mth or an mth-modulating agent is defined as that amount that is effective in modulating a cell's reaction to a biologic stress and/or modulating life span.

In another embodiment, the present invention provides a method for modulating mth gene expression and well as methods for screening for agents which modulate mth gene expression. A cell or subject is contacted with an agent suspected or known to have mth gene expression modulating activity. The change in mth gene expression is then measured as compared to a control or standard sample. The control or standard sample can be the baseline expression of the cell or subject prior to contact with the agent. An agent which modulates mth gene expression may be a polynucleotide for example. The polynucleotide may be an antisense, a triplex agent, a ribozyme, or a double-stranded interferring RNA. For example, an antisense may be directed to the structural gene region or to the promoter region of mth. The agent may be an agonist, antagonist, peptide, peptidomimetic, antibody, or chemical.

Double-stranded interferring RNA molecules are especially useful in the present invention. Such molecules act to inhibit expression of a target gene. For example, double-stranded RNA molecules can be injected into a target cell or organism to inhibit expression of a gene and the resultant gene products activity. It has been found that such double-stranded RNA molecules are more effective at inhibiting expression than either RNA strand alone. (Fire et al., *Nature*, 1998, 19:391(6669):806–11).

When a disorder is associated with abnormal expression of mth, a therapeutic approach which directly interferes with the translation of mth messages into protein is possible. Alternatively, similar methodology may be used to study mth gene activity. For example, antisense nucleic acid, double-stranded interferring RNA or ribozymes could be used to bind to the mth mRNA or to cleave it. Antisense RNA or DNA molecules bind specifically with a targeted gene's RNA message, interrupting the expression of that gene's protein product. The antisense binds to the messenger RNA forming a double stranded molecule which cannot be translated by the cell. Antisense oligonucleotides of about 15–25 nucleotides are preferred since they are easily synthesized and have an inhibitory effect just like antisense RNA molecules. In addition, chemically reactive groups, such as iron-linked ethylenediaminetetraacetic acid (EDTA-Fe) can be attached to an antisense oligonucleotide, causing cleavage of the RNA at the site of hybridization. These and other uses of antisense methods to inhibit the in vitro translation of genes are well known in the art (Marcus-Sakura, *Anal. Biochem.*, 172:289, 1988).

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target MTH-producing cell. The use of antisense methods to inhibit the in vitro translation of genes is well known in the art (Marcus-Sakura, *Anal. Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1:227, 1991; Helene, *Anticancer Drug Design*, 6:569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

These and other uses of antisense methods to inhibit the in vivo translation of genes are well known in the art (e.g., De Mesmaeker, et al., *Curr. Opin. Struct. Biol.*, 5:343, 1995; Gewirtz, A. M., et al., *Proc. Natl. Acad. Sci. U.S.A.*, 93:3161, 1996b; Stein, C. A., *Chem. and Biol.* 3:319, 1996).

Delivery of antisense, triplex agents, ribozymes, competitive inhibitors, double-stranded interferring RNA and the like can be achieved using a recombinant expression vector such as a chimeric virus or a colloidal dispersion system or by injection. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a polynucleotide sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Since recombinant retroviruses are defective, they require assistance in order to produce infectious vector particles.

This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest which will bind to another compound, such as a receptor.

The agents useful in the method of the invention can be administered, for in vivo application, parenterally by injection or by gradual perfusion over time. Administration may be intravenously, intraperitoneally, intramuscularly, subcutaneously, intracavity, or transdermally. For in vitro studies the agents may be added or disolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

Pharmaceutical Compositions

It is envisioned that methods of the present invention can be used to treat pathologies associated with stress disorders. Therefore, the present invention encompasses methods for ameliorating a disorder associated with MTH, including treating a subject having the disorder, at the site of the disorder, with a MTH reactive agent. Generally, the terms "treating", "treatment" and the like are used herein to mean affecting a subject, tissue or cell to obtain a desired pharmacologic and/or physiologic effect. The effect may be prophylactic in terms of completely or partially preventing a disease or sign or symptom thereof, and/or may be therapeutic in terms of a partial or complete cure for an infection or disease and/or adverse effect attributable to the infection or disease. "Treating" as used herein covers any treatment of, or prevention of, an infection or disease in an invertebrate, a vertebrate, a mammal, particularly a human, and includes:

(a) preventing the disease from occurring in a subject that may be predisposed to the disease, but has not yet been diagnosed as having it;

(b) inhibiting the disease, i.e., arresting its development; or (c) relieving or ameliorating the disease, i.e., cause regression of the disease.

However, it should be recognized that the compositions and methods described herein, can be used to bring about a desired result (e.g., an increase in life span or decrease in susceptibility to a biological stress) in the absence of a disease or disorder.

Thus, the invention includes various pharmaceutical compositions useful for ameliorating symptoms attributable to a MTH-associated disorder. The pharmaceutical compositions according to the invention are prepared by bringing an antibody against MTH, a polypeptide or peptide derivative of MTH, a MTH mimetic, or a MTH-binding agent according to the present invention into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences,* 15th ed. Easton: Mack Publishing Co., 1405–1412, 1461–1487 (1975) and *The National Formulary XIV.,* 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's *The Pharmacological Basis for Therapeutics* (7th ed.).

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the subject, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, *Science,* 249: 1527, (1990); Gilman et al. (eds.) (1990), each of which is herein incorporated by reference.

In one embodiment, the invention provides a pharmaceutical composition useful for administering a MTH polypeptide, or nucleic acid encoding a MTH polypeptide, to a subject in need of such treatment. "Administering" the pharmaceutical composition of the present invention may be accomplished by any means known to the skilled artisan. Preferably a "subject" refers to a mammal, most preferably a human, but may be any organism.

The MTH protein or antibody can be administered parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water.

Screening Assay for Compounds that Affect MTHs

In another embodiment, the invention provides a method for identifying a compound which modulates mth expression or activity including incubating components comprising the compound and a MTH polypeptide, or a recombinant cell expressing a MTH polypeptide, under conditions sufficient to allow the components to interact and determining the affect of the compound on the expression or activity of the gene or polypeptide, respectively. The term "affect", as used herein, encompasses any means by which mth gene expression or protein activity can be modulated. Such compounds can include, for example, polypeptides, peptidomimetics, chemical compounds and biologic agents as described below.

Incubating includes conditions which allow contact between the test compound and MTH, a cell expressing MTH or nucleic acid encoding MTH. Contacting includes in solution and in solid phase. The test ligand(s)/compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/— Technology,* 3:1008–1012, 1985), oligonucleotide ligation assays (OLAs) (Landegren, et al., *Science,* 241:1077, 1988), and the like. Molecular techniques for DNA analysis have been reviewed (Landegren, et al., *Science,* 242:229–237, 1988).

Thus, the method of the invention includes combinatorial chemistry methods for identifying chemical compounds that bind to MTH or affect MTH expression or activity. By providing for the production of large amounts of a MTH, one can identify ligands or substrates that bind to, modulate, affect the expression of, or mimic the action of a MTH. For example, a polypeptide may have biological activity associated with the wild-type protein, or may have a loss of function mutation due to a point mutation in the coding sequence, substitution, insertion, deletion and scanning mutations.

Areas of investigation are the development of therapeutic treatments. The screening identifies agents that provide modulation of MTH function in targeted organisms. Of particular interest are screening assays for agents that have a low toxicity for humans. A wide variety of assays may be used for this purpose, including labeled in vitro protein-protein binding assays, protein-DNA binding assays, electrophoretic mobility shift assays, immunoassays for protein binding, and the like. The purified protein may also be used for determination of three-dimensional crystal structure, which can be used for modeling intermolecular interactions, for example.

The term "agent" as used herein describes any molecule, e.g. protein or pharmaceutical, with the capability of altering or mimicking the physiological function or expression of a MTH. Generally, a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification and amidification to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors and anti-microbial agents may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Detection of mth in vivo and in vitro

In a further embodiment, the invention provides a method of detecting mth or a mth-associated disorder in a subject including contacting a cell component containing mth with a reagent which binds to the cell component. The cell component can be nucleic acid, such as DNA or RNA, or it can be protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other labels suitable for binding to an antibody or nucleic acid probe, or will be able to ascertain such, using routine experimentation.

For purposes of the invention, an antibody or nucleic acid probe specific for mth may be used to detect the presence of MTH polypeptide (using antibody) or polynucleotide (using nucleic acid probe) in biological fluids or tissues. Any specimen containing a detectable amount of MTH antigen or polynucleotide can be used. For example, specimens of this invention include blood, urine, cerebrospinal fluid, synovial fluid or any tissue.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific anti-hapten antibodies.

Alternatively, MTH polypeptide can be used to detect antibodies to MTH polypeptide in a specimen. The MTH of the invention is particularly suited for use in immunoassays in which it can be utilized in liquid phase or bound to a solid phase carrier. In addition, MTH used in these assays can be detectably labeled in various ways.

Examples of immunoassays which can utilize the MTH of the invention are competitive and noncompetitive immunoassays in either a direct or indirect format. Examples of such immunoassays are the radioimmunoassay (RIA), the sandwich (immunometric assay) and the Western blot assay. Detection of antibodies which bind to the MTH of the invention can be done utilizing immunoassays which run in either the forward, reverse, or simultaneous modes, including immunohistochemical assays on physiological samples. The concentration of MTH which is used will vary depending on the type of immunoassay and nature of the detectable label which is used. However, regardless of the type of immunoassay which is used, the concentration of MTH utilized can be readily determined by one of ordinary skill in the art using routine experimentation.

The MTH of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding MTH or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to MTH of the invention may be present in various biological fluids and tissues. Any sample containing a detectable amount of antibodies to MTH can be used. Typically, a sample is a liquid such as urine, saliva, cerebrospinal fluid, blood, serum and the like, or a solid or semi-solid such as tissue, feces and the like.

The monoclonal antibodies of the invention, directed toward MTH, are also useful for the in vivo detection of antigen. The detectably labeled monoclonal antibody is given in a dose which is diagnostically effective. The term "diagnostically effective" means that the amount of detectably labeled monoclonal antibody is administered in sufficient quantity to enable detection of MTH antigen for which the monoclonal antibodies are specific.

The concentration of detectably labeled monoclonal antibody which is administered should be sufficient such that the binding to those cells, body fluid, or tissue having MTH is detectable compared to the background. Further, it is desirable that the detectably labeled monoclonal antibody be rapidly cleared from the circulatory system in order to give the best target-to-background signal ratio.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used to monitor the course of amelioration of a stress or MTH-associated disorder. Thus, by measuring the increase or decrease of MTH polypeptide present in various body fluids or tissues, it would be possible to determine whether a particular therapeutic regiment aimed at ameliorating the disorder is effective.

In another embodiment, nucleic acid probes can be used to identify mth nucleic acid from a specimen obtained from a subject. Examples of specimens from which nucleic acid sequence encoding mth can be derived include insect, human, swine, porcine, feline, canine, equine, murine, cervine, caprine, lupine, leporidine and bovine species.

Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.* 9:879, 1981).

In an embodiment of the invention, purified nucleic acid fragments containing intervening sequences or oligonucleotide sequences of 10–50 base pairs are radioactively labeled. The labeled preparations are used to probe nucleic acid from a specimen by the Southern hybridization technique. Nucleotide fragments from a specimen, before or after amplification, are separated into fragments of different molecular masses by gel electrophoresis and transferred to filters that bind nucleic acid. After exposure to the labeled probe, which will hybridize to nucleotide fragments containing target nucleic acid sequences, binding of the radioactive probe to target nucleic acid fragments is identified by autoradiography (see *Genetic Engineering*, 1, ed. Robert Williamson, Academic Press, (1981), 72–81). Alternatively, nucleic acid from the specimen can be bound directly to filters to which the radioactive probe selectively attaches by binding nucleic acids having the sequence of interest. Specific sequences and the degree of binding is quantitated by directly counting the radioactive emissions.

Where the target nucleic acid is not amplified, detection using an appropriate hybridization probe may be performed directly on the separated nucleic acid. In those instances where the target nucleic acid is amplified, detection with the appropriate hybridization probe would be performed after amplification.

For the most part, the probe will be detectably labeled with an atom or inorganic radical, most commonly using radionuclides, but also heavy metals can be used. Conveniently, a radioactive label may be employed. Radioactive labels include $^{32}P$, $^{125}I$, $^{3}H$, $^{14}C$, $^{111}In$, $^{99m}Tc$, or the like. Any radioactive label may be employed which provides for an adequate signal and has sufficient half-life. Other labels include ligands, which can serve as a specific binding pair member for a labeled ligand, and the like. A wide variety of labels routinely employed in immunoassays can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an a $^{32}P$-dNTP or terminal phosphate hydrolysis with alkaline phosphatase followed by labeling with radioactive $^{32}P$ employing $^{32}P$-NTP and T4 polynucleotide kinase. Alternatively, nucleotides can be synthesized where one or more of the elements present are replaced with a radioactive isotope, e.g., hydrogen with tritium. If desired, complementary labeled strands can be used as probes to enhance the concentration of hybridized label.

Where other radionucleotide labels are involved, various linking groups can be employed. A terminal hydroxyl can be esterified, with inorganic acids, e.g., $^{32}P$ phosphate, or $^{14}C$ organic acids, or else esterified to provide linking groups to the label. Alternatively, intermediate bases may be substituted with activatable linking groups that can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2, 3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports that can be used in the method of the invention.

The nucleic acid from a specimen can be cloned and then spotted or spread onto a filter to provide a plurality of individual portions (plaques). The filter is an inert porous solid support, e.g., nitrocellulose. Any cells (or phage) present in the specimen are treated to liberate their nucleic acid. The lysing and denaturation of nucleic acid, as well as the subsequent washings, can be achieved with an appropriate solution for a sufficient time to lyse the cells and denature the nucleic acid. For lysing, chemical lysing will conveniently be employed, as described previously for the lysis buffer. Other denaturation agents include elevated temperatures, organic reagents, e.g., alcohols, amides, amines, ureas, phenols and sulfoxides or certain inorganic ions, e.g., thiocyanate and perchlorate.

After denaturation, the filter is washed in an aqueous buffered solution, such as Tris, generally at a pH of about 6 to 8, usually 7. One or more washings may be involved, conveniently using the same procedure as employed for the lysing and denaturation. After the lysing, denaturing, and washes have been accomplished, the nucleic acid spotted filter is dried at an elevated temperature, generally from about 50° C. to 70° C. Under this procedure, the nucleic acid is fixed in position and can be assayed with the probe when convenient.

Pre-hybridization may be accomplished by incubating the filter with the hybridization solution without the probe at a mildly elevated temperature for a sufficient time to thoroughly wet the filter. Various hybridization solutions may be employed, comprising from about 20% to 60% volume, preferably 30%, of an inert polar organic solvent. A common hybridization solution employs about 50% formamide, about 0.5 to 1M sodium chloride, about 0.05 to 0.1M sodium citrate, about 0.05 to 0.2% sodium dodecylsulfate, and minor amounts of EDTA, ficoll (about 300–500 kDa), polyvinylpyrrolidone, (about 250–500 kDa) and serum albumin. Also included in the hybridization solution will generally be from about 0.5 to 5 mg/ml of sonicated denatured DNA, e.g., calf thymus of salmon sperm; and optionally from about 0.5 to 2% wt/vol glycine. Other additives may also be included, such as dextran sulfate of from about 100 to 1,000 kDa and in an amount of from about 8 to 15 weight percent of the hybridization solution.

The particular hybridization technique is not essential to the invention. Other hybridization techniques are described by Gall and Pardue, (*Proc. Natl. Acad. Sci.* 63:378, 1969); and John, et al., (*Nature,* 223:582, 1969). As improvements are made in hybridization techniques they can readily be applied in the method of the invention.

The amount of labeled probe present in the hybridization solution will vary widely, depending upon the nature of the label, the amount of the labeled probe that can reasonably bind to the filter, and the stringency of the hybridization. Generally, substantial excess over stoichiometric concentrations of the probe will be employed to enhance the rate of binding of the probe to the fixed target nucleic acid.

In nucleic acid hybridization reactions, the conditions used to achieve a particular level of stringency will vary, depending on the nature of the nucleic acids being hybridized. For example, the length, degree of complementarity, nucleotide sequence compound (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

After the filter has been contacted with a hybridization solution at a moderate temperature for a period of time sufficient to allow hybridization to occur, the filter is then introduced into a second solution having analogous concentrations of sodium chloride, sodium citrate and sodium dodecylsulfate as provided in the hybridization solution. The time the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

The label may also comprise a fluorescent moiety that can then be probed with a specific fluorescent antibody. Horseradish peroxidase enzyme can be conjugated to the antibody to catalyze a chemiluminescent reaction. Production of light can then be seen on rapid exposure to film.

Growth Promotion of Cultured Cells by mth

In another embodiment, the invention provides a method for supplementing a culture system with mth or an mth-modulating agent (e.g., an antibody, antisense or ribozyme molecule) in order to promote the production and maintenance of an insect or mammalian cell or cell line. The medium used in the culture system is preferably a commonly used liquid tissue culture medium. The medium can be free of serum and supplemented with various defined components which allow the insect or mammalian cell to proliferate. Mth or an mth-modulating agent is useful for supplementing any culture media well known in the art, such as Grace's insect cell medium or Dulbecco's minimal essential media (DMEM), which contains appropriate amino acids, vitamins, inorganic salts, a buffering agent, and an energy source. Purified molecules, which include hormones, growth factors, transport proteins, trace elements, vitamins, and substratum-modifying factors are added to the media to replace biological fluids.

Transgenic Organisms

The present invention also contemplates transgenic non-human organisms, including invertebrates, vertebrates and mammals. For purposes of the subject invention, these animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene integrated into the chromosomes of somatic cells.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (Biotechnology, 12 Jan. 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention include, for example, bovine, porcine, ovine and avian animals (e.g., cow, pig, sheep, chicken, turkey). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. The use of zygotes as a target for gene transfer has a major advantage in that in most cases the injected DNA will be incorporated into the host gene before the first cleavage (Brinster et al., *Proc. Natl. Acad. Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the subject invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad. Sci. USA* 82:6927–6931, 1985; Van der Putten, et al., *Proc. Natl. Acad. Sci USA* 82:6148–6152, 1985). Transfection is easily and efficiently obtained by culturing the blastomeres on a monolayer of virus-producing cells (Van der Putten, supra; Stewart, et al., *EMBO J.* 6:383–388, 1987). Alternatively, infection can be performed at a later stage. Virus or virus-producing cells can be injected into the blastocoele (D. Jahner et al., Nature 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. Nature 292:154–156, 1981; M. O. Bradley et al., Nature 309: 255–258, 1984; Gossler, et al., Proc. Natl. Acad. Sci USA 83: 9065–9069, 1986; and Robertson et al., Nature 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., Science 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode mth, and include mth-sense, antisense, dominant negative encoding polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete or partial loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

In one embodiment, the transgene comprises DNA antisense to the coding sequence for MTH. In another embodiment, the transgene comprises DNA encoding an antibody which is able to bind to MTH. Where appropriate, DNA sequences that encode proteins having MTH activity but differ in nucleic acid sequence due to the degeneracy of the genetic code may also be used herein, as may truncated forms, allelic variants and interspecies homologues.

The invention also includes animals having heterozygous mutations in mth or partial inhibition of mth function or expression. Partial loss of function leads to an increase in resistance to biological stress, increase in the mass of the organism and an increase in life span. One of skill in the art would readily be able to determine if a particular mutation or if an antisense molecule was able to partially inhibit mth. For example, in vitro testing may be desirable initially by comparison with wild-type or untreated mth (e.g., comparison of northern blots to examine a decrease in expression).

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny (G0) are crossbred to produce offspring (G1) which are analyzed for transgene expression by Northern blot analysis of tissue samples. To be able to distinguish expression of like-species transgenes from expression of the animals endogenous mth gene(s), a marker gene fragment can be included in the construct in the 3' untranslated region of the transgene and the Northern probe designed to probe for the marker gene fragment. The serum levels of mth can also be measured in the transgenic animal to establish appropriate expression. Expression of the mth transgenes, thereby decreasing the mth in the tissue and serum levels of the transgenic animals.

Transgenic organisms of the invention are highly useful in the production of organisms having increased mass for food stuff. For example, bovine, porcine and other animals commonly used for food stuff can be produced using the techniques described above having one allele of mth "knockout" resulting in a heterozygosity. Such organism will demonstrate an increase in mass, for example an increase in fat or muscle mass. In addition, such organisms are useful in the study of age dependence on gene expression as well as age dependence on learning ability. For example, the transgenic or mutant flies of the invention can be used to study the effect on learning during aging. Due to the increased life span of organisms heterozygous for mth, the learning ability of the organism will be affected. Conditioned behavior in such mutant animals can be studied (see, Quinn et al., Proc. Natl, Acad. Sci. USA, 1974, 71(3):708–12).

Kits for Detection of MTH

The materials for use in the method of the invention are ideally suited for the preparation of a kit. Such a kit may comprise a carrier means being compartmentalized to receive one or more container means such as vials, tubes, and the like, each of the container means comprising one of the separate elements to be used in the method. For example, one of the container means may comprise a MTH binding reagent, such as an antibody or nucleic acid. A second container may further comprise MTH polypeptide. The constituents may be present in liquid or lyophilized form, as desired.

One of the container means may comprise a probe which is or can be detectably labeled. Such probe may be an antibody or nucleotide specific for a target protein, or fragments thereof, or a target nucleic acid, or fragment thereof, respectively, wherein the target is indicative, or correlates with, the presence of MTH. For example, oligonucleotide probes of the present invention can be included in a kit and used for examining the presence of mth nucleic acid, as well as the quantitative (relative) degree of binding of the probe for determining the occurrence of specific strongly binding (hybridizing) sequences, thus indicating the likelihood for a subject having a cell growth-associated pathology.

The kit may also contain a container comprising a reporter-means, such as a biotin-binding protein, such as avidin or streptavidin, bound to a reporter molecule, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the target nucleic acid sequence, such as a mth nucleic acid sequence, this can be accomplished using oligonucleotide(s) that are primers for amplification. These oligonucleotide primers are based upon identification of the flanking regions contiguous with the target nucleotide sequence.

The kit may also include a container containing antibodies which bind to a target protein, or fragments thereof. Thus, it is envisioned that antibodies which bind to MTH, or fragments thereof, can be included in a kit.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLES

Example 1

Generation and Identification of Mutants

Figure 1:
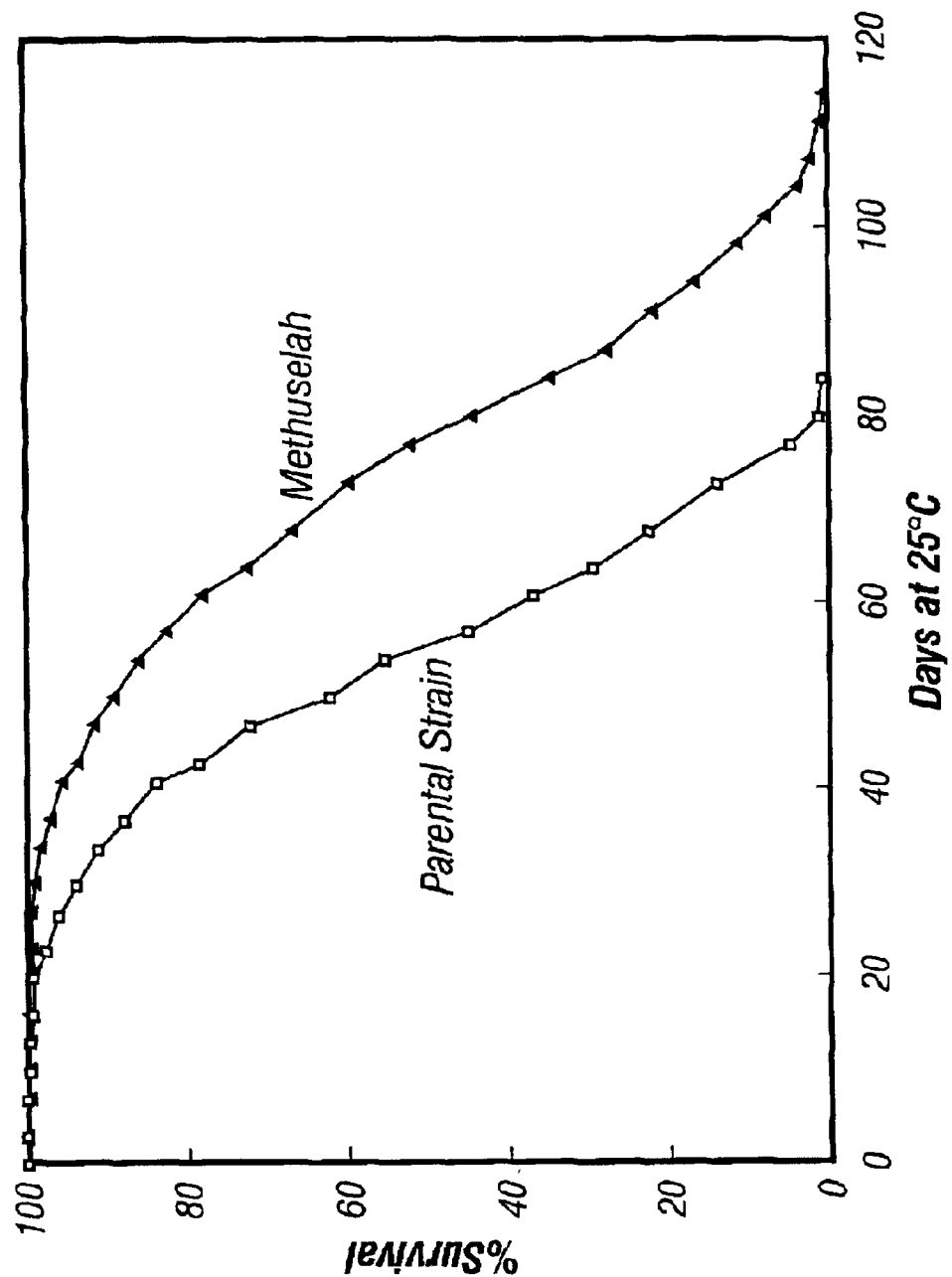
FIG. 1 shows the life span extension effects of Methuselah. Male flies of the parental strain (white[1118]) and Methuselah (homozygous for the P-element insertion) were maintained in a constant temperature, humidity, and 12/12-hour dark/light cycle environment. Flies were transferred to fresh food vials containing standard cornmeal agar medium and scored for survival every three to four days. The average life span for w[1118] and mth were 57 and 77 days, respectively. The numbers of flies tested were 876 for w[1118] and 783 for mth.

A set of P-element insertion lines was generated (E. Bier et al., Genes Dev. 3, 1273–1287 (1989); Spradling et al., Science, 218, 341–347 (1982)) and screened for ones that outlived the parent strain (white$^{1118}$). Because flies live for months at ambient laboratory temperature, the screen was conducted at 29° C. to accelerate the process. Methuselah (mth), was isolated by its increase in lifespan. The life extension was confirmed at the standard temperature of 25° C., at which stocks in the laboratory are maintained. At that temperature, flies homozygous for this P-element live, on the average, 35% longer (FIG. 1).

Example 2

Stress Resistance

Figure 2C:
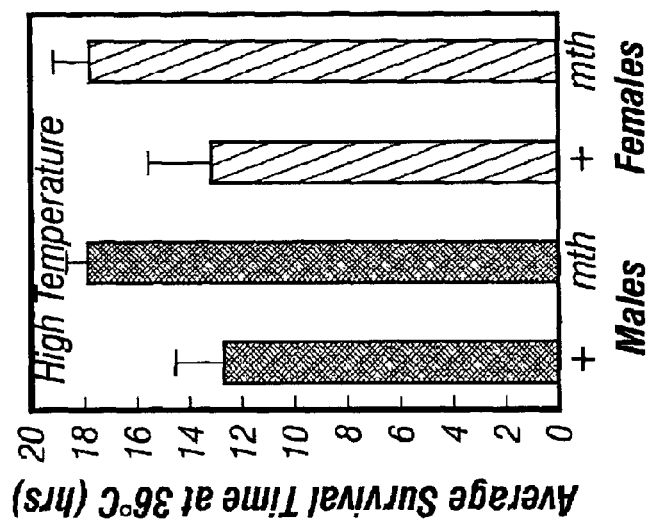
FIG. 2 shows the stress responses in Methuselah flies. Flies homozygous for the mth mutation were compared with those containing the corresponding wild-type allele. Newly eclosed flies were sex-segregated, distributed 20 per vial, and maintained in fresh cornmeal food vials for 2–5 days before testing. Genotypes and sexes are indicated. A. Paraquat resistance. Flies (age two days) were starved for 6 hours, then transferred to vials (2.5 cm×9.3 cm) containing two 2.4 cm glass fiber filter circles (Whatman) wetted with 20 mM paraquat (Sigma) in 5% sucrose solution, and survival scored at 25° C. B. Starvation test. Flies (age two days) were transferred to vials containing filters moisturized with 0.2 ml of distilled water.

The ability of mth flies to resist stress was then examined. As shown in FIG. 2A, mth mutant flies were more resistant to dietary paraquat, a bipyridinium salt which, upon intake by the cell, is reduced to paraquat radical, subsequently giving rise to the original paraquat ion plus superoxide anion (Ashton et al., Mode of Action of Insecticide, John Wiley Interscience, New York, 1973). At a concentration of 20 mM administered by feeding in 5% sucrose solution, paraquat rendered normal males sluggish by 12 hours; at 48 hours, nearly 90% were dead. In contrast, mth males were still active at 24 hours, and at 48 hours more than 50% were still alive. Similar observations were made by Arking et al., Dev. Genet., 12, 362–370 (1991), on a long-lived strain of Drosophila derived by selection, in which lifespan extension accompanied increased paraquat resistance. Transgenic Drosophila carrying extra copies of SOD and catalase, two primary components of the defense system against reactive oxygen species, had significant increase of lifespan (Orr et al., Science, 263, 1128–1120 (1994)). Flies transgenic for the human SOD1 gene also displayed increased lifespan and paraquat resistance, the degree of effect correlating with dosage of the transgene (Parks et al., Nature Genetics, 19, 171–174 (1998)). Although, Applicants are not under any obligation to explain the mechanism of action of mth, mth may have a higher capacity for modulating free-radical activity in the free-radical defense system.

Figure 2B:
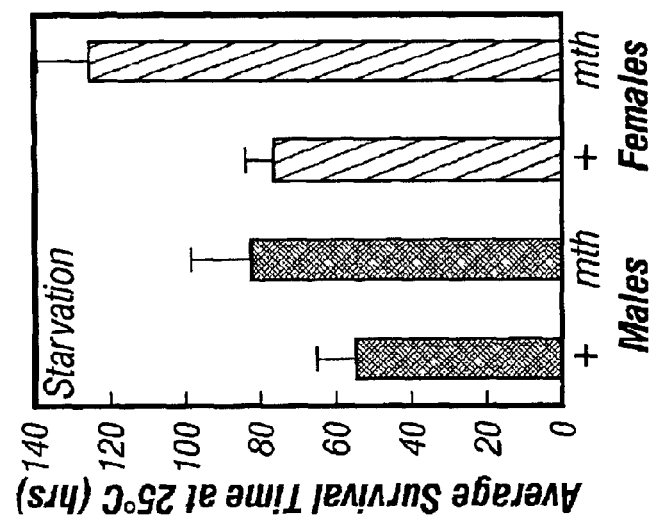
Figure 2A:
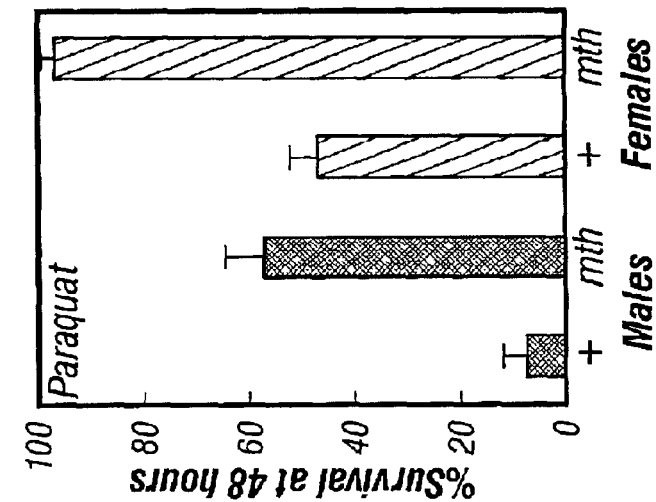

In the starvation test, mth showed over 50% increase in average survival time over the parent strain (FIG. 2B). Females were significantly more resistant than males, suggesting that their larger body weight may contribute to resistance. (Service et al., Physiol. Zool., 58, 380–389 (1985)) reported that, in a Drosophila stock selectively bred for postponed senescence, resistance to starvation and lipid content were higher than the baseline stock. In C. elegans, the mutant daf-2, which exhibits marked increase in longevity, had extensive fat accumulation when grown at 25° C. (Kimura et al., Science, 277, 942–946 (1997)); it was suggested that a higher metabolic capacity of the daf-2 worm plays a central role in its longevity.

The results of exposure to high temperature are shown in FIG. 2C. At 36° C., mth mutant flies survived longer. There was little difference between flies of different sexes, consistent with the observation of Service et al., Physiol. Zool., 58, 380–389 (1985). Heat shock proteins, a class of molecular chaperones, are thought to counter stress-induced detrimental effects during aging (Heydari et al., Proc. Natl. Acad. Sci. USA 92, 10408–10412 (1995)). In a transgenic fly which harbored 12 additional copies of the heat-inducible hsp70 gene, there was a positive correlation between increased life expectancy and elevated hsp70 protein expression (Tatar et al., Nature, 390, 30 (1997)). Correspondingly, in the long-lived C. elegans mutants, daf-2 and age-1, resistance to thermal stress was higher than that in control animals (Lithgow et al., J. Gerontol., 49, B270–B276 (1994); Lithgow et al., Proc. Natl. Acad. Sci. USA 92, 7540–7544 (1995)). Although the inventors are under no duty to explain the mechanism of function of mth, the increased thermotolerance of mth may result from higher expression of heat shock proteins and related molecular chaperones.

Example 3

Identification of Mutant Sequence

To generate P-element insertion lines, females carrying 8 copies of P{lacW} on a compound X chromosome (C(1) RM) were crossed with ry Ki P{ry* D2-3}, which carries the transposase. Female progeny were then crossed individually with w$^{1118}$. New P-element insertions on autosomes were identified by red eye color in male progeny. In any cross which generated progeny having different degrees of red eye color, suggestive of multiple insertions, we chose a single female with lighter eye color and back-crossed it to w$^{1118}$ for several generations, until the color was homogenous. Each insertion was mapped to a chromosome by the use of balancers, tested for homozygous viability and fertility, and established as an independent line. By Southern blots of mth genomic DNA, probed by the ampicillin resistance gene contained in the P-element construct used to generate mutant lines. To generate P-element insertion lines, females carrying 8 copies of P{lacW} (E. Biers et al., supra) on a compound X chrmosome (C(1)RM) were crossed with ry Ki P{ry* D2-3}, which carries the transposase. Female progeny were then crossed individually with w$^{1118}$. New P-element insertions on autosomes were identified by red eye color in male progeny. In any cross which generated progeny having different degrees of red eye color, suggestive of multiple insertions, we chose a single female with lighter eye color and back-crossed it to w$^{1118}$ for several generations, until the color was homogenous. Each insertion was mapped to a chromosome by the use of balancers, tested for homozygous viability and fertility, and established as an independent line. It was confirmed that mth carries a single P-element insertion in the genome. Genetic mapping indicated that it is inserted in the third chromosome. By crossing mth flies to flies harboring the specific transposase, a line was generated in which the P-element was precisely excised from the insertion site (as determined by PCR; see below). To excise the P-element, mth females were crossed with ry kiP{ry* D2-3}. The male jump-starters were then crossed to w;TM3/TM6. Progeny with white eyes were made homozygous and lines established. Two alleles were homozygous lethal prior to the L1 larval stage; those lines were thus maintained over the third chromosome balancers, TM3 or TM6. Eight lines obtained in this manner had lifespans reverted to that of the parent strain, indicating that the phenotype in mth was specifically caused by P-element insertion. The precise-excision strains were used as controls throughout the study; they behaved similarly to the parental strain in stress resistance as well, indicating that the P-element insertion was responsible for both aspects of the phenotype.

Two other lines also isolated had imprecise excisions of the P-element, resulting in DNA deletion adjacent to the insertion site. Both of these lines, likely representing null alleles of the mth gene, displayed embryonic lethality in homozygotes, suggesting that the gene also plays an essential role in development. Flies heterozygous for the P-element over an imprecise excision allele were more resistant to stress than those homozygous for the P-element, indicating that the mutation created by the P-element insertion is a hypomorphic allele.

Example 4

The Methuselah Gene

Genomic DNA adjacent to the P-element insertion site in the mth mutant fly was retrieved by plasmid rescue technique (Hamilton et al., *Methods in cell biology.* L. S. B. Golstein eds., Academic press, Inc., San Diego, 1994, vol. 44, pp. 81–94). Plasmid rescue from *Drosophila* genomic DNA was performed according to Hamilton et al., supra. Pst I and EcoR I digestion were used to clone upstream and downstream genomic fragments (FIG. 3A) Among the 21 upstream and 15 downstream clones, all within each group had identical restriction fragment patterns and nucleotide sequences (up to at least 500 bases) flanking each end of the plasmid rescue vector, confirming that there was only a single P-element insertion in mth. Analysis of the upstream DNA sequence by BLAST search (Altschul et al., *J. Mol. Biol.*, 215, 403–410 (1990)) revealed two homologous sequences (Clones LD08316 and GM02553) in the EST database of the Berkeley *Drosophila* Genome Project (BDGP). The GM02553 clone, albeit containing regions with 670 identity to the mth nucleotide sequence, had 17 gaps in the alignment. In contrast, the 747-nucleotide partial sequence of LD08316 in the BDGP database displayed greater than 99% identity to the upstream sequence, without any gap. The calculated smallest sum probability of the BLAST search was 1.5e-137, well within the range of identical sequences.

Figure 3A:
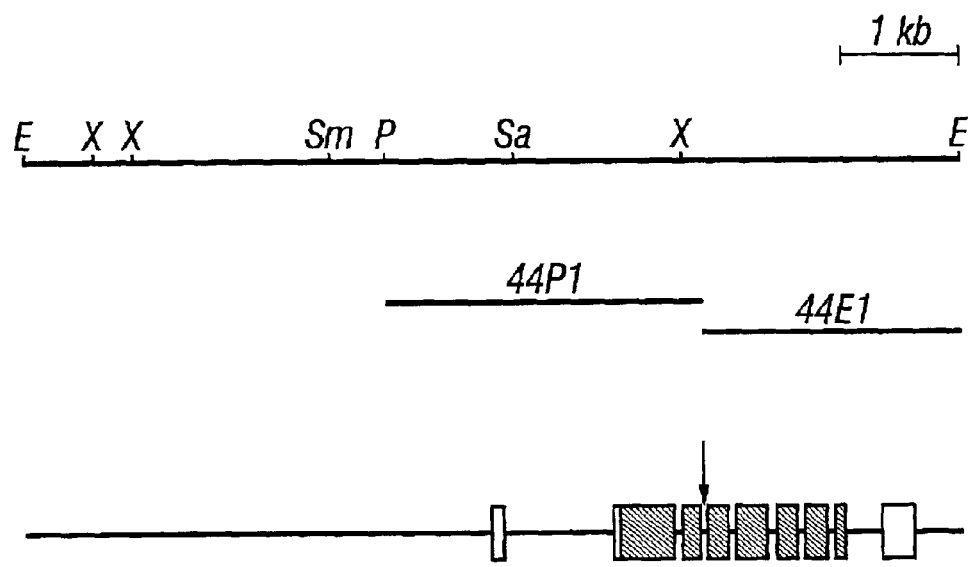

A LD08316 clone was obtained via the BDGP and its full sequence determined(1948 nucleotides; see FIG. 3B), finding that its sequence corresponded with the downstream genomic sequence of mth except for a small (less than 1%) sequence disparity, probably due to polymorphism among different melanogaster strains. The cDNA was then used as a probe to isolate the full-length mth genomic DNA. Three Pi plasmids (DS05332, DS03799, and DS06692) from the BDPG contained the genomic region of the mth gene. These P1 clones have a common contig. DS00539, which maps at 61C on the third chromosome (BDGP database). A corresponding 7.9-kilobase EcoR I fragment from DS06692 was subcloned into pBluescript vector and the full-length sequence determined (FIG. 3A). The P-element insertion in the third intron of the mth gene, may reduce the level of gene expression by interfering with RNA splicing, without eliminating the gene function. By polymerase chain reaction and sequencing, we confirmed that the precise-excision strains had restored the normal sequence across the insertion site.

Figure 3C:
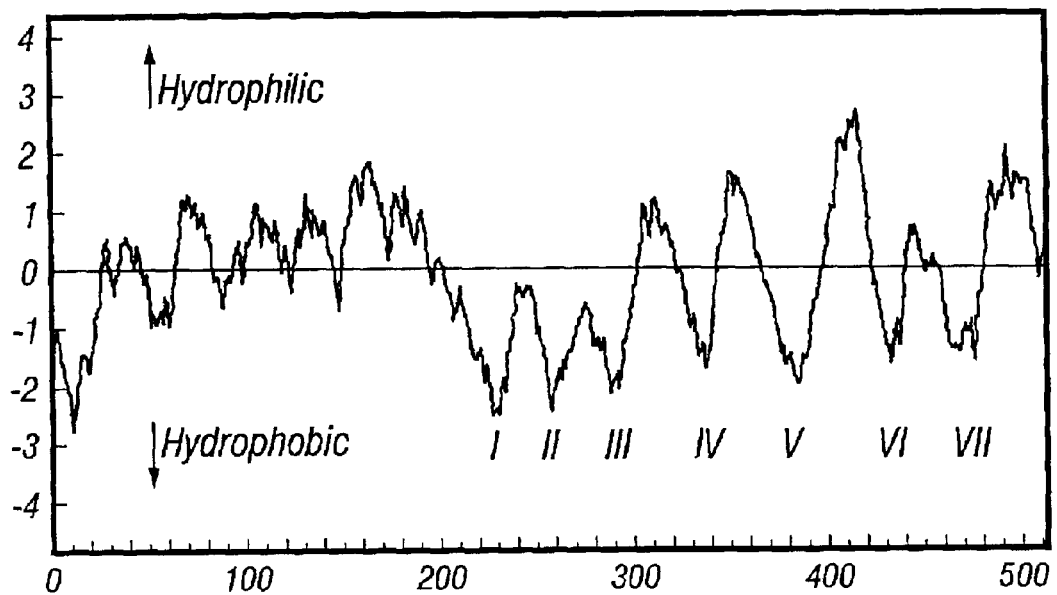
Figure 3B-1:
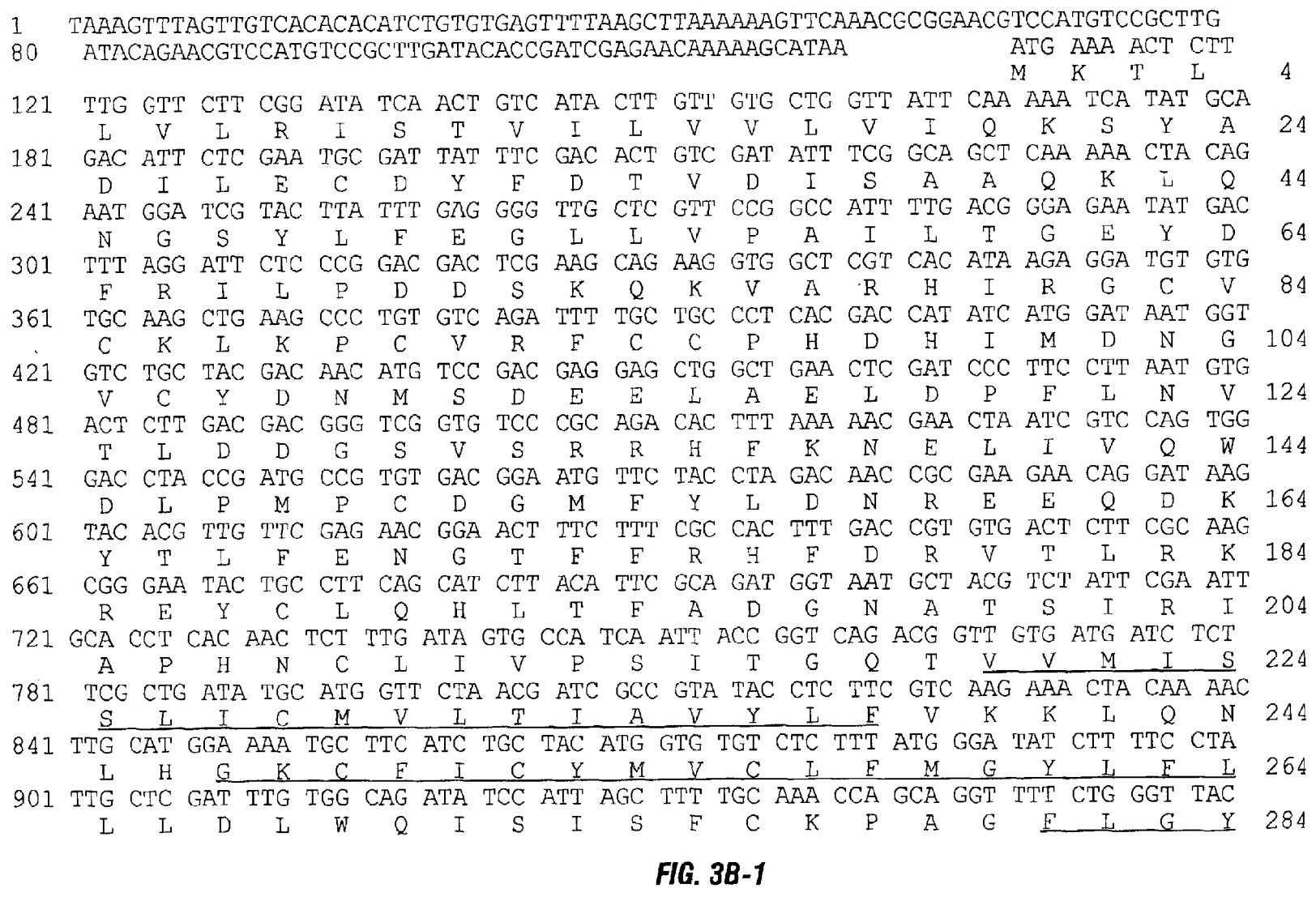
Figure 3B-2:
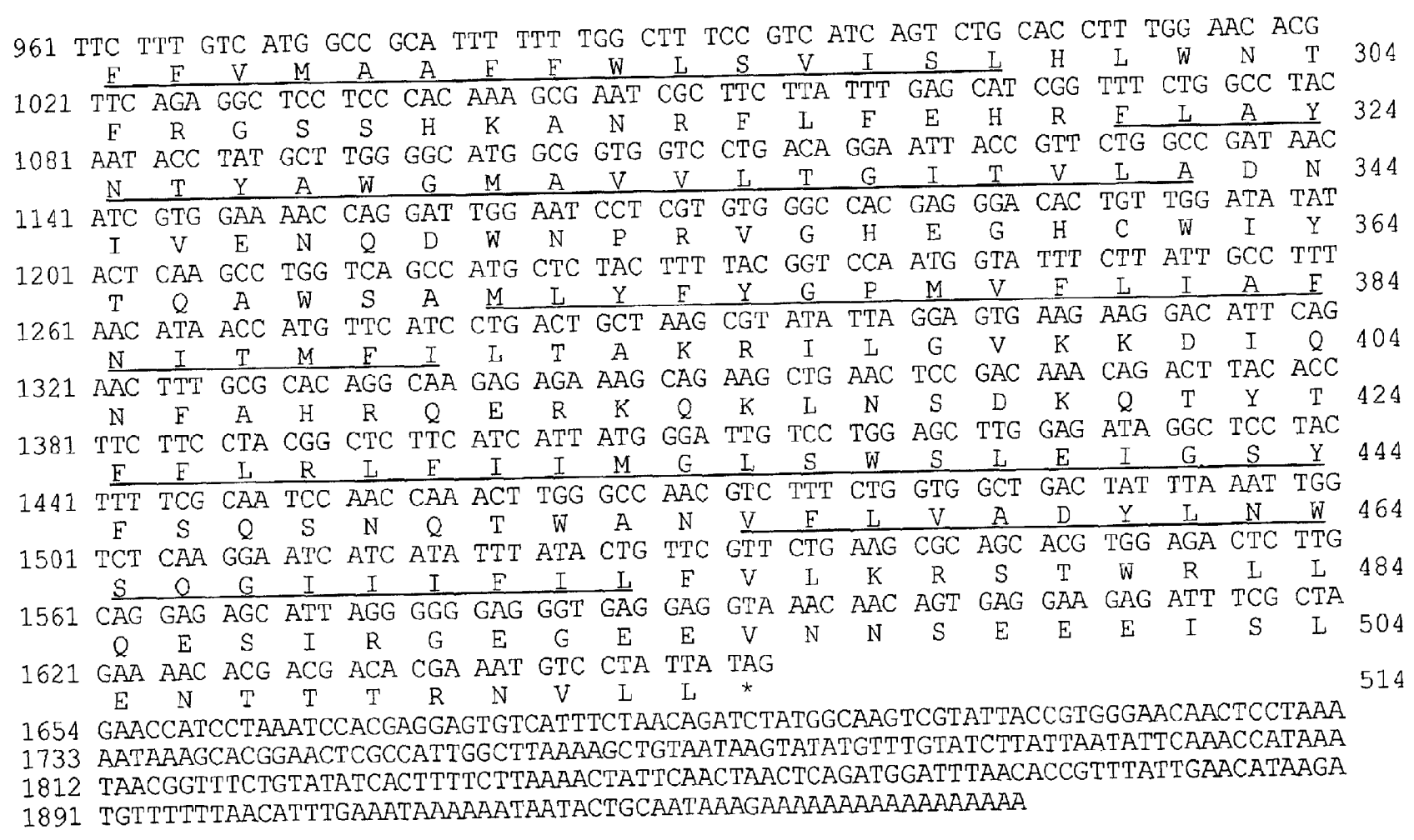

The mth cDNA encodes a single, uninterrupted open reading frame (FIG. 3B). The predicted protein sequence has a leader peptide plus seven hydrophic regions suggestive of transmembrane (TM) domains (FIG. 3C). A gapped BLAST search (Altschul et al., *Nucleic Acids Res.,* 25, 3389–3402 (1997)) of this sequence showed homology to a variety of GTP-binding regulatory protein (G-protein)-coupled receptors (FIG. 4A). G-protein-coupled receptor was also predicted by the Blocks Search program (Henikoff & Henikoff, *Genomics,* 19, 97–107 (1994)). The amino acid residues between TM5 and TM6, especially those near the transmembranes, are highly basic, a feature shared by many G-protein-linked receptors and known, in some cases, to interact directly with G-proteins (Kobilka et al., *Science,* 240, 1310–1316 (1988)). Interestingly, homology was found mainly in the TM regions. The N-terminal segment prior to the first TM domain was not found to share homology with any known sequence. Therefore, despite the structural conservation in the TM regions, the overall homology score with any given sequence was diminished. The mth gene appears to represent a novel member of the seven-TM protein superfamily.

G-protein-coupled receptors are involved in a remarkably diverse array of biological activities, including neurotransmission, hormone physiology, drug response, morphogenetic differentiation, embryonic development, and transduction of stimuli such as light and odorants (Watson & Arkinstall, *The G-protein linked receptor facts book* (Academic Press, London, 1994)). The data indicate that mth is a G-protein-coupled receptor involved in stress response and biological aging. By regulating an associated G-protein and thus its downstream pathway, the normal mth gene may maintain homeostasis and metabolism, playing a central role in modulating molecular events in response to stress. The embryonic lethality of all the null alleles demonstrates that at least some activity of the mth gene is essential for survival. When mutated, the intermediate level of expression of a hypomorphic allele might adjust response to stress in a way that is more favorable for survival, whereas full expression of the normal gene exceeds the optimum value. The delicate balance among the embryonic lethality of a null allele, enhance longevity of a hypomorphic allele, and the normal wild phenotype suggests that the level of mth gene expression is an important component of the system controlling lifespan. Investigation of the gene's function and associated pathways, should lead to better understanding of mechanisms relevant to aging.

Since lifespan and stress response are closely related, genetic screening by stress resistance provides an effective alternative to the much slower direct screening for lifetime. The ability of the mth fly to resist various kinds of stress is notable, since there are likely to exist differences in pathways of response to individual forms of stress. For instance, in the process of this study, we have also obtained a Drosphila mutant line that is resistant to starvation, but not heat.

Example 5

Expression of Methuselah

In order to determine the expression of MTH in wildtype (e.g., $w^{1118}$) flies compared to mth mutant flies, labeled antisense probes were used. The antisense probes were derived from the cDNA sequence for mth, as described above, and enzymatically labeled (although any type of label known in the art can be used). FIG. 5 shows the comparison of mth expression in $w^{1118}$ flies compared to the Methuselah mutants in the head region of the fly. A reduction of about 10-fold was seen in expression of MTH in the mutant flies compared to the controls. FIG. 6, shows similar expression in the thoracic region of the fly.

FIG. 7 shows the results of an RNA protection assay using a labeled antisense RNA to the mth cDNA sequence. The gel compares the expression of mth in wildtype flies and mth mutant flies (P+/mth+). Lane 5 represents RNA from mth mutant adult flies, demonstrating a reduction in expression of mth in P+/mth+ Drosophila compared to lane 6. Lane 6 shows RNA from wildtype Drosophila (mth+/mth+). Lane 7 and 8 demonstrate the difference in expression of mth in mutant flies (lane 7) compared to wildtype (lane 8) in Drosophila embryos.

Example 6

Monoclonal Antibodies to MTH

A monoclonal antibody was raised against the MTH sequence AHRQERKQKLNSDK (amino acids 407–420 of SEQ ID NO:2) using techniques well known to those of skill in the art, as described above.

Using the monoclonal antibody, above, localization and expression of mth in Drosophila mth-mutants and wildtype flies was performed. The antibody was incubated with sections of Drosophila and developed with anti-mouse secondary antibody and FITC. FIG. 8 demonstrates the localiation and expression. The left series of panels represents wildtype flies (i.e., panels A, C, E, and G) and the right series of panels represents the mth mutant flies (i.e., panels B, D, F, and H). Panels A–B are from the trunk thoracic muscles of the flies. Panels C–D are from the ventral layer of the thoracic region. Panels E–F are from leg muscles of the flies. Panels G–H are from the proboscis muscle. The mth mutant flies have a reduction of MTH protein in all segments of the Drosophila tested.

What is claimed is:

1. An isolated antibody that binds to a polypeptide selected from the group consisting of:

a) a polypeptide encoded by a nucleic acid molecule which hybridizes in 0.1×SSC at 68° C. to a nucleic acid molecule consisting of SEQ ID NO:1, wherein 1) the polypeptide is a GPCR, 2) failure to express the polypeptide results in embryonic lethality in *Drosophila,* and 3) hypomorphic expression of the polypeptide increases resistance to heat stress in *Drosophila;* and b) a polypeptide consisting of an amino acid sequence which is at least 85% homologous to the amino acid sequence of SEQ ID NO:2, wherein 1) the polypeptide is a GPCR, 2) failure to express the polypeptide results in embryonic lethality in *Drosophila,* and 3) hypomorphic expression of the polypeptide increases resistance to heat stress in *Drosophila,* wherein the antibody binds to the amino acid sequence that is at least 85% homologous to SEQ ID NO:2.

2. The antibody of claim 1, wherein the antibody is polyclonal.

3. The antibody of claim 1, wherein the antibody is monoclonal.

4. An isolated antibody or fragment thereof that binds to:

a) a polypeptide consisting of SEQ ID NO:2;

b) a polypeptide consisting of amino acid residues 1 to 200 of SEQ ID NO:2;

c) a polypeptide consisting of an antigenic fragment of SEQ ID NO:2; or d) a polypeptide consisting of a fragment of SEQ ID NO:2 of at least 50 contiguous amino acid residues of SEQ ID NO:2, wherein the antibody or fragment thereof binds to the amino acid sequence of SEQ ID NO:2.

5. The antibody of claim 4, which is a monoclonal antibody.

6. The antibody of claim 4, which is a polyclonal antibody.

7. The antibody of claim 4, which is a humanized antibody.

8. The antibody or fragment thereof of claim 4, which is a human antibody.

9. The antibody or fragment thereof of claim 4, which is a single chain antibody.

10. An isolated antibody or fragment thereof produced by immunizing an animal with a composition comprising a polypeptide selected from the group consisting of:

a) a polypeptide consisting of SEQ ID NO:2;

b) a polypeptide consisting of amino acid residues 1 to 200 of SEQ ID NO:2;
c) a polypeptide consisting of an antigenic fragment of SEQ ID NO:2; or
d) a polypeptide consisting of a fragment of SEQ ID NO:2 of at least 50 contiguous amino acids residues of SEQ ID NO:2,
wherein the antibody specifically binds to the polypeptide comprising SEQ ID NO:2.

11. An isolated antibody that binds to a polypeptide consisting of the amino acid sequence as set forth in SEQ ID NO:2.

12. An isolated antibody that binds the hydrophilic domain of an mth polypeptide between hydrophobic domains five and six of SEQ ID NO:2.

13. An isolated antibody that binds to amino acids 407–420 of SEQ ID NO:2.

14. A composition comprising the antibody of claim 1, 4, 10, 11, 12 or 13 and a pharmaceutically acceptable carrier.

15. A hybridoma cell line that produces an antibody according to claim 1, 4, 11, 12, or 13.

16. A kit comprising an antibody of claim 1, 4, 10, 11, 12, or 13.

* * * * *

SEQUENCE LISTING

<160> NUMBER OF SEQ ID NOS: 6

<210> SEQ ID NO 1
<211> LENGTH: 1972
<212> TYPE: DNA
<213> ORGANISM: Drosophila Melanogaster
<220> FEATURE:
<221> NAME/KEY: CDS
<222> LOCATION: (130)...(1679)

<400> SEQUENCE: 1

```
taaagtttag ttgtcacaca catctgtgtg agttttaagc ttaaaaaaag ttcaaacgcg      60
gaacgtccat gtccgcttga tacagaacgt ccatgtccgc ttgatacacc gatcgagaac     120 aaaaaagca taa atg aaa act ctt ttg gtt ctt cgg ata tca act gtc ata     171
            *   Met Lys Thr Leu Leu Val Leu Arg Ile Ser Thr Val Ile
                 1               5                  10 ctt gtt gtg ctg gtt att caa aaa tca tat gca gac att ctc gaa tgc      219
Leu Val Val Leu Val Ile Gln Lys Ser Tyr Ala Asp Ile Leu Glu Cys
     15                  20                  25 gat tat ttc gac act gtc gat att tcg gca gct caa aaa cta cag aat     267
Asp Tyr Phe Asp Thr Val Asp Ile Ser Ala Ala Gln Lys Leu Gln Asn
 30                  35                  40                  45 gga tcg tac tta ttt gag ggg ttg ctc gtt ccg gcc att ttg acg gga     315
Gly Ser Tyr Leu Phe Glu Gly Leu Leu Val Pro Ala Ile Leu Thr Gly
                 50                  55                  60 gaa tat gac ttt agg att ctc ccg gac gac tcg aag cag aag gtg gct     363
Glu Tyr Asp Phe Arg Ile Leu Pro Asp Asp Ser Lys Gln Lys Val Ala
             65                  70                  75 cgt cac ata aga gga tgt gtg tgc aag ctg aag ccc tgt gtc aga ttt     411
Arg His Ile Arg Gly Cys Val Cys Lys Leu Lys Pro Cys Val Arg Phe
         80                  85                  90
```

```
tgc tgc cct cac gac cat atc atg gat aat ggt gtc tgc tac gac aac      459
Cys Cys Pro His Asp His Ile Met Asp Asn Gly Val Cys Tyr Asp Asn
         95                 100                 105 atg tcc gac gag gag ctg gct gaa ctc gat ccc ttc ctt aat gtg act      507
Met Ser Asp Glu Glu Leu Ala Glu Leu Asp Pro Phe Leu Asn Val Thr
110                 115                 120                 125 ctt gac gac ggg tcg gtg tcc cgc aga cac ttt aaa aac gaa cta atc      555
Leu Asp Asp Gly Ser Val Ser Arg Arg His Phe Lys Asn Glu Leu Ile
                130                 135                 140 gtc cag tgg gac cta ccg atg ccg tgt gac gga atg ttc tac cta gac      603
Val Gln Trp Asp Leu Pro Met Pro Cys Asp Gly Met Phe Tyr Leu Asp
            145                 150                 155 aac cgc gaa gaa cag gat aag tac acg ttg ttc gag aac gga act ttc      651
Asn Arg Glu Glu Gln Asp Lys Tyr Thr Leu Phe Glu Asn Gly Thr Phe
        160                 165                 170 ttt cgc cac ttt gac cgt gtg act ctt cgc aag cgg gaa tac tgc ctt      699
Phe Arg His Phe Asp Arg Val Thr Leu Arg Lys Arg Glu Tyr Cys Leu
    175                 180                 185 cag cat ctt aca ttc gca gat ggt aat gct acg tct att cga att gca      747
Gln His Leu Thr Phe Ala Asp Gly Asn Ala Thr Ser Ile Arg Ile Ala
190                 195                 200                 205 cct cac aac tgt ttg ata gtg cca tca att acc ggt cag acg gtt gtg      795
Pro His Asn Cys Leu Ile Val Pro Ser Ile Thr Gly Gln Thr Val Val
                210                 215                 220 atg atc tct tcg ctg ata tgc atg gtt cta acg atc gcc gta tac ctc      843
Met Ile Ser Ser Leu Ile Cys Met Val Leu Thr Ile Ala Val Tyr Leu
            225                 230                 235 ttc gtc aag aaa cta caa aac ttg cat gga aaa tgc ttc atc tgc tac      891
Phe Val Lys Lys Leu Gln Asn Leu His Gly Lys Cys Phe Ile Cys Tyr
        240                 245                 250 atg gtg tgt ctc ttt atg gga tat ctt ttc cta ttg ctc gat ttg tgg      939
Met Val Cys Leu Phe Met Gly Tyr Leu Phe Leu Leu Leu Asp Leu Trp
    255                 260                 265 cag ata tcc att agc ttt tgc aaa cca gca ggt ttt ctg ggt tac ttc      987
Gln Ile Ser Ile Ser Phe Cys Lys Pro Ala Gly Phe Leu Gly Tyr Phe
270                 275                 280                 285 ttt gtc atg gcc gca ttt ttt tgg ctt tcc gtc atc agt ctg cac ctt     1035
Phe Val Met Ala Ala Phe Phe Trp Leu Ser Val Ile Ser Leu His Leu
                290                 295                 300 tgg aac acg ttc aga ggc tcc tcc cac aaa gcg aat cgc ttc tta ttt     1083
Trp Asn Thr Phe Arg Gly Ser Ser His Lys Ala Asn Arg Phe Leu Phe
            305                 310                 315 gag cat cgg ttt ctg gcc tac aat acc tat gct tgg ggc atg gcg gtg     1131
Glu His Arg Phe Leu Ala Tyr Asn Thr Tyr Ala Trp Gly Met Ala Val
        320                 325                 330 gtc ctg aca gga att acc gtt ctg gcc gat aac atc gtg gaa aac cag     1179
Val Leu Thr Gly Ile Thr Val Leu Ala Asp Asn Ile Val Glu Asn Gln
    335                 340                 345 gat tgg aat cct cgt gtg ggc cac gag gga cac tgt tgg ata tat act     1227
Asp Trp Asn Pro Arg Val Gly His Glu Gly His Cys Trp Ile Tyr Thr
350                 355                 360                 365 caa gcc tgg tca gcc atg ctc tac ttt tac ggt cca atg gta ttt ctt     1275
Gln Ala Trp Ser Ala Met Leu Tyr Phe Tyr Gly Pro Met Val Phe Leu
                370                 375                 380 att gcc ttt aac ata acc atg ttc atc ctg acg gct aag cgt ata tta     1323
Ile Ala Phe Asn Ile Thr Met Phe Ile Leu Thr Ala Lys Arg Ile Leu
            385                 390                 395 gga gtg aag aag gac att cag aac ttt gcg cac agg caa gag aga aag     1371
Gly Val Lys Lys Asp Ile Gln Asn Phe Ala His Arg Gln Glu Arg Lys
```

```
                       400                 405                 410
cag aag ctg aac tcc gac aaa cag act tac acc ttc ttc cta cgg ctc       1419
Gln Lys Leu Asn Ser Asp Lys Gln Thr Tyr Thr Phe Phe Leu Arg Leu
        415                 420                 425 ttc atc att atg gga ttg tcc tgg agc ttg gag ata ggc tcc tac ttt       1467
Phe Ile Ile Met Gly Leu Ser Trp Ser Leu Glu Ile Gly Ser Tyr Phe
430                 435                 440                 445 tcg caa tcc aac caa act tgg gcc aac gtc ttt ctg gtg gct gac tat       1515
Ser Gln Ser Asn Gln Thr Trp Ala Asn Val Phe Leu Val Ala Asp Tyr
                450                 455                 460 tta aat tgg tct caa gga atc atc ata ttt ata ctg ttc gtt ctg aag       1563
Leu Asn Trp Ser Gln Gly Ile Ile Ile Phe Ile Leu Phe Val Leu Lys
            465                 470                 475 cgc agc acg tgg aga ctc ttg cag gag agc att agg ggg gag ggt gag       1611
Arg Ser Thr Trp Arg Leu Leu Gln Glu Ser Ile Arg Gly Glu Gly Glu
        480                 485                 490 gag gta aac aac agt gag gaa gag att tcg cta gaa aac acg acg aca       1659
Glu Val Asn Asn Ser Glu Glu Glu Ile Ser Leu Glu Asn Thr Thr Thr
    495                 500                 505 cga aat gtc cta tta tag ga accatcctaa atccacgagg agtgtcattt           1709
Arg Asn Val Leu Leu  *
510 ctaacagatc tatggcaagt cgtattaccg tgggaacaac tcctaaaaat aaagcacgga     1769 actcgccatt ggcttaaaag ctgtaataag tatatgtttg tatcttatta atattcaaac     1829 cataaataac ggtttctgta tatcactttt cttaaaacta ttcaactaac tcagatggat     1889 ttaacaccgt ttattgaaca taagatgttt tttaacattt gaaataaaaa ataatactgc     1949 aataaaaaaa aaaaaaaaaa aaa                                             1972

<210> SEQ ID NO 2
<211> LENGTH: 514
<212> TYPE: PRT
<213> ORGANISM: Drosophila Melanogaster

<400> SEQUENCE: 2

Met Lys Thr Leu Leu Val Leu Arg Ile Ser Thr Val Ile Leu Val Val
1               5                   10                  15

Leu Val Ile Gln Lys Ser Tyr Ala Asp Ile Leu Glu Cys Asp Tyr Phe
            20                  25                  30

Asp Thr Val Asp Ile Ser Ala Ala Gln Lys Leu Gln Asn Gly Ser Tyr
        35                  40                  45

Leu Phe Glu Gly Leu Leu Val Pro Ala Ile Leu Thr Gly Glu Tyr Asp
    50                  55                  60

Phe Arg Ile Leu Pro Asp Asp Ser Lys Gln Lys Val Ala Arg His Ile
65                  70                  75                  80

Arg Gly Cys Val Cys Lys Leu Lys Pro Cys Val Arg Phe Cys Cys Pro
                85                  90                  95

His Asp His Ile Met Asp Asn Gly Val Cys Tyr Asp Asn Met Ser Asp
            100                 105                 110

Glu Glu Leu Ala Glu Leu Asp Pro Phe Leu Asn Val Thr Leu Asp Asp
        115                 120                 125

Gly Ser Val Ser Arg Arg His Phe Lys Asn Glu Leu Ile Val Gln Trp
    130                 135                 140

Asp Leu Pro Met Pro Cys Asp Gly Met Phe Tyr Leu Asp Asn Arg Glu
145                 150                 155                 160

Glu Gln Asp Lys Tyr Thr Leu Phe Glu Asn Gly Thr Phe Phe Arg His
```

```
                    165                 170                 175
Phe Asp Arg Val Thr Leu Arg Lys Arg Glu Tyr Cys Leu Gln His Leu
            180                 185                 190

Thr Phe Ala Asp Gly Asn Ala Thr Ser Ile Arg Ile Ala Pro His Asn
            195                 200                 205

Cys Leu Ile Val Pro Ser Ile Thr Gly Gln Thr Val Val Met Ile Ser
            210                 215                 220

Ser Leu Ile Cys Met Val Leu Thr Ile Ala Val Tyr Leu Phe Val Lys
225                 230                 235                 240

Lys Leu Gln Asn Leu His Gly Lys Cys Phe Ile Cys Tyr Met Val Cys
                245                 250                 255

Leu Phe Met Gly Tyr Leu Phe Leu Leu Asp Leu Trp Gln Ile Ser
            260                 265                 270

Ile Ser Phe Cys Lys Pro Ala Gly Phe Leu Gly Tyr Phe Val Met
            275                 280                 285

Ala Ala Phe Phe Trp Leu Ser Val Ile Ser Leu His Leu Trp Asn Thr
            290                 295                 300

Phe Arg Gly Ser Ser His Lys Ala Asn Arg Phe Leu Phe Glu His Arg
305                 310                 315                 320

Phe Leu Ala Tyr Asn Thr Tyr Ala Trp Gly Met Ala Val Val Leu Thr
                325                 330                 335

Gly Ile Thr Val Leu Ala Asp Asn Ile Val Glu Asn Gln Asp Trp Asn
                340                 345                 350

Pro Arg Val Gly His Glu Gly His Cys Trp Ile Tyr Thr Gln Ala Trp
                355                 360                 365

Ser Ala Met Leu Tyr Phe Tyr Gly Pro Met Val Phe Leu Ile Ala Phe
370                 375                 380

Asn Ile Thr Met Phe Ile Leu Thr Ala Lys Arg Ile Leu Gly Val Lys
385                 390                 395                 400

Lys Asp Ile Gln Asn Phe Ala His Arg Gln Glu Arg Lys Gln Lys Leu
                405                 410                 415

Asn Ser Asp Lys Gln Thr Tyr Thr Phe Phe Leu Arg Leu Phe Ile Ile
                420                 425                 430

Met Gly Leu Ser Trp Ser Leu Glu Ile Gly Ser Tyr Phe Ser Gln Ser
            435                 440                 445

Asn Gln Thr Trp Ala Asn Val Phe Leu Val Ala Asp Tyr Leu Asn Trp
            450                 455                 460

Ser Gln Gly Ile Ile Phe Ile Leu Phe Val Leu Lys Arg Ser Thr
465                 470                 475                 480

Trp Arg Leu Leu Gln Glu Ser Ile Arg Gly Glu Gly Glu Val Asn
                485                 490                 495

Asn Ser Glu Glu Glu Ile Ser Leu Glu Asn Thr Thr Thr Arg Asn Val
            500                 505                 510
Leu Leu

<210> SEQ ID NO 3
<211> LENGTH: 269
<212> TYPE: PRT
<213> ORGANISM: Drosophila Melanogaster

<400> SEQUENCE: 3

Asn Cys Leu Ile Val Pro Ser Ile Thr Gly Gln Thr Val Val Met Ile
1               5                   10                  15

Ser Ser Leu Ile Cys Met Val Leu Thr Ile Ala Val Tyr Leu Phe Val
            20                  25                  30
```

```
Lys Lys Leu Gln Asn Leu His Gly Lys Cys Phe Ile Cys Tyr Met Val
            35                  40                  45
Cys Leu Phe Met Gly Tyr Leu Phe Leu Leu Asp Leu Trp Gln Ile
 50                  55                  60
Ser Ile Ser Phe Cys Lys Pro Ala Gly Phe Leu Gly Tyr Phe Phe Val
 65                  70                  75                  80
Met Ala Ala Phe Phe Trp Leu Ser Val Ile Ser Leu His Leu Trp Asn
                     85                  90                  95
Thr Phe Arg Gly Ser Ser His Lys Ala Asn Arg Phe Leu Phe Glu His
            100                 105                 110
Arg Phe Leu Ala Tyr Asn Thr Tyr Ala Trp Gly Met Ala Val Val Leu
            115                 120                 125
Thr Gly Ile Thr Val Leu Ala Asp Asn Ile Val Glu Asn Gln Asp Trp
130                 135                 140
Asn Pro Arg Val Gly His Glu Gly His Cys Trp Ile Tyr Thr Gln Ala
145                 150                 155                 160
Trp Ser Ala Met Leu Tyr Phe Tyr Gly Pro Met Val Phe Leu Ile Ala
                165                 170                 175
Phe Asn Ile Thr Met Phe Ile Leu Thr Ala Lys Arg Ile Leu Gly Val
                180                 185                 190
Lys Lys Asp Ile Gln Asn Phe Ala His Arg Gln Glu Arg Lys Gln Lys
            195                 200                 205
Leu Asn Ser Asp Lys Gln Thr Tyr Thr Phe Phe Leu Arg Leu Phe Ile
210                 215                 220
Ile Met Gly Leu Ser Trp Ser Leu Glu Ile Gly Ser Tyr Phe Ser Gln
225                 230                 235                 240
Ser Asn Gln Thr Trp Ala Asn Val Phe Leu Val Ala Asp Tyr Leu Asn
                245                 250                 255
Trp Ser Gln Gly Ile Ile Ile Phe Ile Leu Phe Val Leu
            260                 265

<210> SEQ ID NO 4
<211> LENGTH: 231
<212> TYPE: PRT
<213> ORGANISM: Homosapiens

<400> SEQUENCE: 4

Ser Leu Phe Cys Leu Leu Leu Cys Ile Leu Thr Phe Leu Leu Val Arg
 1               5                  10                  15
Pro Ile Gln Gly Ser Arg Thr Thr Ile His Leu His Leu Cys Ile Cys
            20                  25                  30
Leu Phe Val Gly Ser Thr Ile Phe Leu Ala Gly Ile Glu Asn Glu Gly
            35                  40                  45
Gly Gln Val Gly Leu Arg Cys Arg Leu Val Ala Gly Leu Leu His Tyr
 50                  55                  60
Cys Gly Leu Ala Ala Gly Cys Trp Met Ser Leu Glu Gly Leu Glu Leu
 65                  70                  75                  80
Tyr Phe Leu Val Val Arg Val Phe Gln Gly Gln Gly Leu Ser Thr Arg
                 85                  90                  95
Trp Leu Cys Leu Ile Gly Tyr Gly Val Pro Leu Leu Ile Val Gly Val
            100                 105                 110
Ser Ala Ala Ile Tyr Ser Lys Gly Tyr Gly Arg Pro Arg Tyr Cys Trp
            115                 120                 125
Leu Asp Phe Glu Gln Gly Phe Leu Trp Ser Phe Leu Gly Pro Val Thr
```

```
            130                 135                 140
Phe Ile Ile Leu Cys Asn Ala Val Ile Phe Val Thr Thr Val Trp Lys
145                 150                 155                 160

Leu Thr Gln Lys Phe Ser Glu Ile Asn Pro Asp Met Lys Lys Leu Lys
                165                 170                 175

Lys Ala Arg Ala Leu Thr Ile Thr Ala Ile Ala Gln Leu Phe Leu Leu
            180                 185                 190

Gly Cys Thr Trp Val Phe Gly Leu Phe Ile Phe Asp Asp Arg Ser Leu
            195                 200                 205

Val Leu Thr Tyr Val Phe Thr Ile Leu Asn Cys Leu Gln Gly Ala Phe
210                 215                 220

Leu Tyr Leu Leu His Cys Leu
225                 230

<210> SEQ ID NO 5
<211> LENGTH: 240
<212> TYPE: PRT
<213> ORGANISM: Rattus norvegicus

<400> SEQUENCE: 5

Asn Glu Leu Leu Leu Ser Val Ile Thr Trp Val Gly Ile Val Ile Ser
1               5                   10                  15

Leu Val Cys Leu Ala Ile Cys Ile Ser Thr Phe Cys Phe Leu Arg Gly
            20                  25                  30

Leu Gln Thr Asp Arg Asn Thr Ile His Lys Asn Leu Cys Ile Asn Leu
        35                  40                  45

Phe Leu Ala Glu Leu Leu Phe Leu Val Gly Ile Asp Lys Thr Gln Tyr
50                  55                  60

Glu Val Ala Cys Pro Ile Phe Ala Gly Leu Leu His Tyr Phe Phe Leu
65                  70                  75                  80

Ala Ala Phe Ser Trp Leu Cys Leu Glu Gly Val His Leu Tyr Leu Leu
                85                  90                  95

Leu Val Glu Val Phe Glu Ser Glu Tyr Ser Arg Thr Lys Tyr Tyr Tyr
            100                 105                 110

Leu Gly Gly Tyr Cys Phe Pro Ala Leu Val Val Gly Ile Ala Ala Ala
        115                 120                 125

Ile Asp Tyr Arg Ser Tyr Gly Thr Glu Lys Ala Cys Trp Leu Arg Val
130                 135                 140

Asp Asn Tyr Phe Ile Trp Ser Phe Ile Gly Pro Val Ser Phe Val Ile
145                 150                 155                 160

Val Val Asn Leu Val Phe Leu Met Val Thr Leu His Lys Met Ile Arg
                165                 170                 175

Ser Ser Ser Val Leu Lys Pro Asp Ser Ser Arg Leu Asp Asn Ile Lys
            180                 185                 190

Ser Trp Ala Leu Gly Ala Ile Ala Leu Leu Phe Leu Leu Gly Leu Thr
        195                 200                 205

Trp Ala Phe Gly Leu Leu Phe Ile Asn Lys Glu Ser Val Val Met Ala
210                 215                 220

Tyr Leu Phe Thr Thr Phe Asn Ala Phe Gln Gly Val Phe Ile Phe Val
225                 230                 235                 240

<210> SEQ ID NO 6
<211> LENGTH: 235
<212> TYPE: PRT
<213> ORGANISM: Mus musculus
```

-continued

```
<400> SEQUENCE: 6

Val Ile Ser Leu Val Cys Leu Ala Leu Ala Ile Ala Thr Phe Leu Leu
  1               5                  10                  15

Cys Arg Ala Val Gln Asn His Asn Thr Tyr Met His Leu His Leu Cys
               20                  25                  30

Val Cys Leu Phe Leu Ala Lys Ile Leu Phe Leu Thr Gly Ile Asp Lys
           35                  40                  45

Thr Asp Asn Gln Thr Ala Cys Ala Ile Ile Ala Gly Phe Leu His Tyr
       50                  55                  60

Leu Phe Leu Ala Cys Phe Phe Trp Met Leu Val Glu Ala Val Met Leu
 65                  70                  75                  80

Phe Met Val Arg Asn Leu Lys Val Val Asn Tyr Phe Ser Ser Arg Asn
               85                  90                  95

Ile Lys Met Leu His Leu Cys Ala Phe Gly Tyr Gly Leu Pro Val Leu
               100                 105                 110

Val Val Ile Ile Ser Ala Ser Val Gln Pro Arg Gly Tyr Gly Met His
           115                 120                 125

Asn Arg Cys Trp Leu Asn Thr Glu Thr Gly Phe Ile Trp Ser Phe Leu
    130                 135                 140

Gly Pro Val Cys Met Ile Ile Thr Ile Met Ser Val Leu Leu Ala Trp
145                 150                 155                 160

Thr Leu Trp Val Leu Arg Gln Lys Leu Cys Ser Val Ser Ser Glu Val
               165                 170                 175

Ser Lys Leu Lys Asp Thr Arg Leu Leu Thr Phe Lys Ala Ile Ala Gln
               180                 185                 190

Ile Phe Ile Leu Gly Cys Ser Trp Val Leu Gly Ile Phe Gln Ile Gly
           195                 200                 205

Pro Leu Ala Ser Ile Met Ala Tyr Leu Phe Thr Ile Ile Asn Ser Leu
       210                 215                 220

Gln Gly Ala Phe Ile Phe Leu Ile His Cys Leu
225                 230                 235
```